United States Patent
Carrara et al.

(10) Patent No.: US 7,404,965 B2
(45) Date of Patent: *Jul. 29, 2008

(54) COMPOSITION FOR TRANSDERMAL AND/OR TRANSMUCOSAL ADMINISTRATION OF ACTIVE COMPOUNDS THAT ENSURES ADEQUATE THERAPEUTIC LEVELS

(75) Inventors: Dario Carrara, Buenos Aires (AR); Gabriel Porto, Basel (CH); Jorge Rodriguez, Buenos Aires (AR)

(73) Assignee: Antares Pharma IPL AG, Zug (CH)

( * ) Notice: Subject to any disclaimer, the term of this patent is extended or adjusted under 35 U.S.C. 154(b) by 0 days.

This patent is subject to a terminal disclaimer.

(21) Appl. No.: 11/634,005

(22) Filed: Dec. 4, 2006

(65) Prior Publication Data

US 2007/0098775 A1    May 3, 2007

Related U.S. Application Data

(63) Continuation of application No. 10/343,570, filed as application No. PCT/EP01/09007 on Aug. 3, 2001, now Pat. No. 7,214,381.

(30) Foreign Application Priority Data

Aug. 3, 2000  (WO) .................. PCT/EP00/07533

(51) Int. Cl.
*A61K 9/20* (2006.01)
*A61K 9/70* (2006.01)
*A61F 13/00* (2006.01)

(52) U.S. Cl. ............... 424/400; 424/436; 424/449; 424/464

(58) Field of Classification Search ................. 424/401, 424/46, 436, 449, 464, 400; 514/218, 359, 514/944, 966, 969
See application file for complete search history.

(56) References Cited

U.S. PATENT DOCUMENTS

| | | | |
|---|---|---|---|
| 2,990,332 A | 6/1961 | Keating | 167/65 |
| 3,143,465 A | 8/1964 | Keating | 167/65 |
| 3,989,816 A | 11/1976 | Rajadhyaksha | 424/60 |

(Continued)

FOREIGN PATENT DOCUMENTS

EP    0 249 397    12/1987

(Continued)

OTHER PUBLICATIONS www.rxlist.com.*

(Continued)

*Primary Examiner*—Johann Richter
*Assistant Examiner*—Konata M George
(74) *Attorney, Agent, or Firm*—Winston & Strawn LLP

(57) ABSTRACT

A pharmaceutical composition in the form of a solution, cream, lotion, spray, ointment, gel, aerosol, tablet, suppository or patch device for transdermal or transmucosal administration of alprazolam to a subject, which includes as a permeation enhancing mixture a fatty component in an amount of 0.1% to 20% by weight which is one of (a) a saturated fatty alcohol of formula $CH_3-(CH_2)_n-CH_2OH$, a saturated fatty acid of formula $CH_3-(CH_2)_n-CH_2COOH$, (b) an unsaturated fatty alcohol of formula $CH_3(C_nH_{2(n-1)})-OH$, or (c) a fatty acid of formula $CH_3(C_nH_{2(n-1)})-COOH$, wherein n is an integer of between 8 and 22; and a vehicle that includes a $C_1$-$C_4$ alkanol, a polyalcohol, and water.

13 Claims, 22 Drawing Sheets

U.S. PATENT DOCUMENTS

| | | | |
|---|---|---|---|
| 4,082,881 A | 4/1978 | Chen et al. | 424/241 |
| 4,221,778 A | 9/1980 | Raghunathan | 424/31 |
| 4,315,925 A | 2/1982 | Hussaiin et al. | 424/239 |
| 4,316,893 A | 2/1982 | Rajadhyakshan | 424/180 |
| 4,383,993 A | 5/1983 | Hussaiin et al. | 424/239 |
| 4,390,532 A | 6/1983 | Stuttgen et al. | 424/240 |
| 4,405,616 A | 9/1983 | Rajadhyaksha | 424/60 |
| 4,537,776 A | 8/1985 | Cooper | 514/424 |
| 4,557,934 A | 12/1985 | Cooper | 424/128 |
| 4,568,343 A | 2/1986 | Leeper et al. | 604/896 |
| 4,597,961 A | 7/1986 | Etscorn | 424/448 |
| 4,704,406 A | 11/1987 | Stanislaus et al. | 514/570 |
| 4,764,381 A | 8/1988 | Bodor et al. | 424/449 |
| 4,783,450 A | 11/1988 | Fawzi et al. | 514/78 |
| 4,808,411 A | 2/1989 | Lu et al. | 424/441 |
| 4,832,953 A | 5/1989 | Campbell et al. | 424/448 |
| 4,863,970 A | 9/1989 | Patel et al. | 514/784 |
| 4,883,660 A | 11/1989 | Blackman et al. | 424/78 |
| 4,952,560 A | 8/1990 | Kigasawa et al. | 514/2 |
| 4,956,171 A | 9/1990 | Chang | 424/449 |
| 4,973,468 A | 11/1990 | Chiang et al. | 424/449 |
| 5,041,439 A | 8/1991 | Kasting et al. | 514/227.2 |
| 5,053,227 A | 10/1991 | Chiang et al. | 424/448 |
| 5,059,426 A | 10/1991 | Chiang et al. | 424/449 |
| 5,071,657 A | 12/1991 | Oloff | 424/486 |
| 5,112,842 A | 5/1992 | Zierenberg et al. | 514/367 |
| 5,128,138 A | 7/1992 | Blank | 424/449 |
| 5,134,127 A | 7/1992 | Stella et al. | 514/58 |
| 5,164,190 A | 11/1992 | Patel et al. | 424/448 |
| 5,178,879 A | 1/1993 | Adekunle et al. | 424/484 |
| 5,188,825 A | 2/1993 | Iles et al. | 424/78.1 |
| 5,225,189 A | 7/1993 | Pena | 424/70 |
| 5,232,703 A | 8/1993 | Blank | 424/449 |
| 5,238,933 A | 8/1993 | Catz | 514/236.2 |
| 5,352,457 A | 10/1994 | Jenkins | 424/448 |
| 5,371,005 A | 12/1994 | Fujishiro et al. | 435/190 |
| 5,376,645 A | 12/1994 | Stella et al. | 514/58 |
| 5,453,279 A | 9/1995 | Lee et al. | 424/448 |
| 5,527,832 A | 6/1996 | Chi et al. | 514/772.4 |
| 5,532,278 A | 7/1996 | Aberg et al. | 514/617 |
| 5,580,574 A * | 12/1996 | Behl et al. | 424/449 |
| 5,601,839 A | 2/1997 | Quan et al. | 424/448 |
| 5,602,017 A | 2/1997 | Fujishiro et al. | 435/190 |
| 5,603,947 A | 2/1997 | Wong et al. | 424/448 |
| 5,629,021 A | 5/1997 | Wright | 424/489 |
| 5,633,008 A | 5/1997 | Osborne et al. | 424/448 |
| 5,658,587 A | 8/1997 | Santus et al. | 424/448 |
| 5,660,839 A | 8/1997 | Allec et al. | 424/401 |
| 5,662,890 A | 9/1997 | Punto et al. | 424/59 |
| 5,665,560 A | 9/1997 | Fujishiro et al. | 435/11 |
| 5,677,346 A | 10/1997 | Aberg et al. | 51/617 |
| 5,716,638 A | 2/1998 | Touitou | 424/450 |
| 5,719,197 A | 2/1998 | Kanios et al. | 514/772.6 |
| 5,731,303 A | 3/1998 | Hsien | 514/183 |
| 5,736,577 A | 4/1998 | Aberg et al. | 514/617 |
| 5,783,207 A | 7/1998 | Stanley et al. | 424/440 |
| 5,785,991 A | 7/1998 | Burkoth et al. | 424/448 |
| 5,798,242 A | 8/1998 | Fujishiro et al. | 435/190 |
| 5,814,659 A | 9/1998 | Elden | 514/452 |
| 5,831,035 A | 11/1998 | Timms | 530/389.1 |
| 5,834,010 A | 11/1998 | Quan et al. | 424/448 |
| 5,843,482 A | 12/1998 | Rhodes et al. | 424/653 |
| 5,846,983 A | 12/1998 | Sandborn et al. | 514/343 |
| 5,855,905 A | 1/1999 | Oettel et al. | 424/426 |
| 5,855,920 A | 1/1999 | Chein | 424/568 |
| 5,891,462 A | 4/1999 | Carrara | 424/449 |
| 5,900,250 A | 5/1999 | Lee et al. | 424/448 |
| 5,904,931 A | 5/1999 | Lipp | 424/449 |
| 5,922,349 A | 7/1999 | Elliesen et al. | 424/449 |
| 5,932,243 A | 8/1999 | Fricker et al. | 424/450 |
| 5,935,604 A | 8/1999 | Illum | 424/501 |
| 5,945,405 A | 8/1999 | Spanton et al. | 514/29 |
| 5,968,919 A | 10/1999 | Samour | 514/177 |
| 6,008,192 A | 12/1999 | Al Razzak et al. | 514/11 |
| 6,034,079 A | 3/2000 | Sandberg et al. | 514/225.8 |
| 6,060,077 A | 5/2000 | Meignant | 424/434 |
| 6,071,959 A | 6/2000 | Rhodes et al. | 514/535 |
| 6,096,733 A | 8/2000 | Lubkin | 514/182 |
| 6,123,961 A | 9/2000 | Aberg | 424/468 |
| 6,124,355 A | 9/2000 | Guittard et al. | 514/534 |
| 6,133,248 A | 10/2000 | Stella | 514/58 |
| 6,153,216 A | 11/2000 | Cordes | 424/449 |
| 6,165,497 A | 12/2000 | Osborne et al. | 424/448 |
| 6,166,044 A | 12/2000 | Sandborn et al. | 514/343 |
| 6,180,803 B1 | 1/2001 | Piasco et al. | 552/150 |
| 6,238,689 B1 | 5/2001 | Rhodes et al. | 424/436 |
| 6,267,985 B1 | 7/2001 | Chen et al. | 424/451 |
| 6,284,234 B1 | 9/2001 | Niemiec | 424/78.07 |
| 6,299,900 B1 | 10/2001 | Reed et al. | 424/449 |
| 6,309,843 B1 | 10/2001 | Timms | 435/7.1 |
| 6,319,913 B1 | 11/2001 | Mak et al. | 514/179 |
| 6,383,471 B1 | 5/2002 | Chen et al. | 424/45 |
| 6,417,205 B1 | 7/2002 | Cooke et al. | 514/343 |
| 6,426,078 B1 | 7/2002 | Bauer et al. | 424/401 |
| 6,432,446 B2 | 8/2002 | Aberg | 424/468 |
| 6,440,454 B1 | 8/2002 | Santoro et al. | 424/449 |
| 6,444,234 B1 | 9/2002 | Kirby et al. | 424/725 |
| 6,465,005 B1 | 10/2002 | Biali et al. | 424/449 |
| 6,476,012 B2 | 11/2002 | Hochberg | 514/182 |
| 6,479,076 B2 | 11/2002 | Blank | 424/484 |
| 6,497,897 B2 | 12/2002 | Hidaka et al. | 424/449 |
| 6,503,894 B1 | 1/2003 | Dudley et al. | 514/178 |
| 6,545,046 B2 | 4/2003 | Sherratt et al. | 514/534 |
| 6,586,000 B2 | 7/2003 | Luo et al. | 424/449 |
| 6,596,740 B2 | 7/2003 | Jones | 514/343 |
| 6,743,441 B2 | 6/2004 | Sanders et al. | 424/448 |
| 6,818,226 B2 | 11/2004 | Reed et al. | 424/449 |
| 6,828,336 B2 | 12/2004 | Walling | 514/343 |
| 6,911,475 B1 | 6/2005 | Cesaro et al. | 514/567 |
| 6,923,983 B2 | 8/2005 | Morgan et al. | 424/448 |
| 6,929,801 B2 | 8/2005 | Klose et al. | 424/448 |
| 6,951,846 B2 | 10/2005 | Hartell et al. | 514/58 |
| 6,995,265 B2 | 2/2006 | Comins et al. | 546/14 |
| 7,029,692 B1 | 4/2006 | Bracht | 424/449 |
| 7,087,241 B2 | 8/2006 | Sanders et al. | 424/449 |
| 7,198,801 B2 | 4/2007 | Carrara et al. | 424/449 |
| 7,214,381 B2 * | 5/2007 | Carrara et al. | 424/400 |
| 2001/0023261 A1 | 9/2001 | Ryoo | 514/772 |
| 2001/0031787 A1 | 10/2001 | Hsu et al. | 514/534 |
| 2001/0033870 A1 | 10/2001 | Luo | 424/688 |
| 2001/0038855 A1 | 11/2001 | Desjardin et al. | 424/468 |
| 2002/0147236 A1 | 10/2002 | Sanders et al. | 514/540 |
| 2002/0183296 A1 | 12/2002 | Dudley et al. | 514/177 |
| 2003/0022877 A1 | 1/2003 | Dudley | 514/177 |
| 2003/0050292 A1 | 3/2003 | Dudley | 514/177 |
| 2003/0095926 A1 | 5/2003 | Dugger, III | 424/43 |
| 2003/0139384 A1 | 7/2003 | Dudley | 514/177 |
| 2003/0143278 A1 | 7/2003 | DiPiano et al. | 424/489 |
| 2003/0147926 A1 | 8/2003 | Ebert et al. | 424/400 |
| 2003/0175329 A1 | 9/2003 | Azarnoff et al. | 424/449 |
| 2003/0181430 A1 | 9/2003 | Gray et al. | 514/170 |
| 2003/0199426 A1 | 10/2003 | Carrara et al. | 514/2 |
| 2003/0222105 A1 | 12/2003 | Lee et al. | 222/382 |
| 2003/0232072 A1 | 12/2003 | Dudley et al. | 424/449 |
| 2004/0002482 A1 | 1/2004 | Dudley et al. | 514/169 |
| 2004/0139990 A1 | 7/2004 | Wachter et al. | 134/25.4 |
| 2004/0198706 A1 | 10/2004 | Carrara et al. | 514/169 |
| 2004/0219197 A1 | 11/2004 | Carrara et al. | 424/449 |
| 2005/0142175 A1 | 6/2005 | Langguth et al. | 424/449 |
| 2006/0027278 A1 | 2/2006 | Kurmis | 140/123.5 |

| | | | |
|---|---|---|---|
| 2006/0153905 A1 | | 7/2006 | Carrara et al. ............. 424/449 |

FOREIGN PATENT DOCUMENTS

| | | |
|---|---|---|
| EP | 0 261 429 A1 | 3/1988 |
| EP | 0 267 617 A1 | 5/1988 |
| EP | 0 271 983 A1 | 6/1988 |
| EP | 0 279 977 A2 | 8/1988 |
| EP | 0 367 431 A1 | 5/1990 |
| EP | 0250125 B1 | 9/1991 |
| EP | 0 526 561 B1 | 2/1993 |
| EP | 0325613 B1 | 9/1993 |
| EP | 0 672 422 A1 | 3/1994 |
| EP | 0409383 B1 | 4/1994 |
| EP | 0435200 B1 | 7/1995 |
| EP | 785211 A1 | 7/1997 |
| EP | 785212 A1 | 7/1997 |
| EP | 0 811 381 A1 | 12/1997 |
| EP | 0491803 B1 | 7/1999 |
| EP | 0804926 B1 | 10/1999 |
| EP | 0655900 B1 | 3/2000 |
| EP | 0719538 B1 | 11/2000 |
| EP | 0814776 B1 | 7/2001 |
| EP | 0643963 B1 | 11/2001 |
| EP | 0868187 B1 | 12/2001 |
| EP | 0859793 B1 | 2/2002 |
| EP | 1089722 B1 | 5/2002 |
| EP | 0802782 B1 | 2/2003 |
| EP | 1 323 430 A2 | 7/2003 |
| EP | 1 323 431 A2 | 7/2003 |
| EP | 1 325 752 A2 | 7/2003 |
| FR | 2518879 | 12/1981 |
| FR | 2776191 | 9/1999 |
| JP | 09176049 | 7/1997 |
| WO | WO 92/08730 | 5/1992 |
| WO | WO 94/06437 | 3/1994 |
| WO | WO 95/18603 A1 | 7/1995 |
| WO | WO 95/29678 A1 | 11/1995 |
| WO | WO 97/03676 | 2/1997 |
| WO | WO 97/29735 A1 | 8/1997 |
| WO | WO 97/34607 | 9/1997 |
| WO | WO 97/38726 | 10/1997 |
| WO | WO 98/17316 A1 | 4/1998 |
| WO | WO 98/37879 | 9/1998 |
| WO | WO 99/20257 | 4/1999 |
| WO | WO 99/24041 | 5/1999 |
| WO | WO 99/48477 | 9/1999 |
| WO | WO 01/80796 A1 | 11/2001 |
| WO | WO 02/11768 A1 | 2/2002 |
| WO | WO 02/22132 | 2/2002 |
| WO | WO 02/17967 A1 | 3/2002 |
| WO | WO 2004/080413 A2 | 9/2004 |
| WO | WO 2005/039531 A1 | 5/2005 |

OTHER PUBLICATIONS

Budavari et al., The Merck Index, 1996, Merk Research Laboratories, 12th Edition, pp. 253 and 269.
Kotiyan et al., "Eudragits:Role as crystallization inhibitors in drug-in-adhesive transdermal systems of estradiol," European Journal of Pharmaceutics and Biopharmaceutics 52: 173-180 (2001).
Lipp, "Selection and use of crystallization inhibitors for matrix-type transdermal drug-delivery systems containing sex steroids," J. Pharm. Pharmacol. 50: 1343-1349 (1998).
Moser et al., "Passive skin penetration enhancement and its quantification in vitro," European Journal of Pharmaceutics and Biopharmaceutics 52: 103-112 (2001).
Mura et al., "Evaluation of transcutol as a clonazepam transdermal permeation enhancer from hydrophilic gel formulations," European Journal of Pharmaceutical Sciences 9: 365-372 (2000).
R. Panchagnula et al., "Development and evaluation of an intracutaneous depot formulation of corticosteroids using transcutol as a cosolvent: in-vitro, ex-vivo and in-vivo rat studies," J. Pharm. Pharmacol. 1991, 43: 609-614.
L. Pavliv et al., "Topical formulation development of a novel thymidylate synthase inhibitor for the treatment of psoriasis," International Journal of Pharmaceutics 1994, 105: 227-233.
W.A. Ritschel et al., "In vitro skin penetration of griseofulvin in rat and human skin from an ointment dosage form," Arzneimittelforschung. 1988, 38(11): 1630-1632.
W.A. Ritschel et al., "Use of sorption promoters to increase systemic absorption of coumarin from transdermal drug delivery systems," Arzneimittelforschung. 1988, 38(12): 1774-1777.
W.A. Ritschel et al., "Development of an intracutaneous depot for drugs," Skin Pharmacol. 1991, 4:235-245.
J. Rojas, "Optimization of binary and ternary solvent systems in the percutaneous absorption of morphine base," S.T.P. Pharma Sciences 1991, 1(1): 70-75.
E. Touitou, "Enhanced permeation of theophylline through the skin and its effect on fibroblast proliferation," International Journal of Pharmaceutics 1991, 70: 159-166.
A. Watkinson, "Aspects of the transdermal delivery of prostaglandins," International Journal of Pharmaceutics 1991, 74: 229-236.
M. Yazdanian et al., "The effect of diethylene glycol monoethyl ether as a vehicle for topical delivery of ivermectin," Veterinary Research Communications 1995, 19(4): 309-319.
English Abstract NLM2807923 XP-002337932,"Promoting Penetration Of Locally Applied Substances By Urea".
P. Karande and S. Mitragotri, "High Throughput Screening of Transdermal Formulations," Pharmaceutical Research, 2002, 19(5): 655-660.
J. Fang et al., XP-0007999490, "Effect of Adhesive and Drug reservoir on in vitro transdermal delivery of Nocotine," Pharmazie, Die, Govi Verlag, Eschborn, De, (1999), 54(2): 154-155.
David W. Osborne et al., XP 002337808, "Skin Penetration Enhancers Cited in the Technical Literature".
A.C. Williams et al., XP 000645464,"Urea Analogues In Propylene Glycol As Penetration Enhancers In Human Skin", International Journal of Pharmaceutics, vol. 36, pp. 43-50 (1989).
Oxytrol Data Sheet.
Koichi Takahashi et al., "Effect of Vehicles on Diclofenac Permeation across Excised Rat Skin", Biol. Pharm. Bull., vol. 18, No. 4, pp. 571-575 (1995).
"New Drug Application: Elestrin, estradiol, Treatment for Postmenopausal Symptoms. BioSante Pharmaceuticals Announces Bio-E-Gel NDA Submission," Internet article, [online], Feb. 16, 2006; retrieved from the Internet: URL:http://www.drugs.com/nda/elestrin_060216.html (retrieved on Sep. 18, 2007).
US 6,214,374, 04/2001, Schmirier et al. (withdrawn)

* cited by examiner

Graphic III
*E2 serum levels*
*Mean values +/- SEM*

Graphic IV
LN serum levels
Mean values +/- SEM

Graphic V
Testosterone in vitro flux

Graphic VII
*Combi Gel Testosterone*

Graphic VIII
Testosterone serum levels each 24 h before gel application

Graphic X
Testosterone and Norethindrone Acetate permeated

COMPOSITION FOR TRANSDERMAL AND/OR TRANSMUCOSAL ADMINISTRATION OF ACTIVE COMPOUNDS THAT ENSURES ADEQUATE THERAPEUTIC LEVELS

CROSS-REFERENCE TO RELATED APPLICATIONS

This application is a continuation of application Ser. No. 10/343,570 filed May 19, 2003, now U.S. Pat. No. 7,214,381, which is the US national stage of International Application PCT/EP01/09007 filed Aug. 3, 2001, which claims the benefit of International application PCT/EP00/07533 filed Aug. 3, 2000.

FIELD OF THE INVENTION

The present invention relates to a novel composition for transdermal administration of different active compounds or a mixture thereof. The invention reveals a pharmaceutical formulation with good cosmetic properties and low irritation potential, useful for the systemic treatment of diverse diseases by transdermal or transmucosal route. A formulation that administers the active drug(s), at a permeation rate that would ensure therapeutically effective systemic concentration, containing defined amounts of chemicals that minimize the barrier characteristics of the most uppermost layer of the epidermis and provide sustained permeation rate. Said chemicals are: fatty alcohols such as lauryl alcohol, n-decanol, oleyl alcohol, etc. and diethylene glycol monoethyl ether in a ternary vehicle composite consisting of ethanol, propylene glycol and water.

BACKGROUND OF THE INVENTION

It is well known that many drugs taken orally, are destroyed on the first pass through the liver. It is also well known that when many drugs are taken orally, their rate of absorption into the body is not constant. In view of such difficulties, a number of different drug delivery systems have been developed.

The transdermal or transmucosal route for delivery of drugs provides many advantages, and transdermal or transmucosal systems for delivering a wide variety of drugs are described in U.S. Pat. Nos. 5,785,991; 4,764,381; 4,956,171; 4,863,970; 5,453,279; 4,883,660; 5,719,197 or EP patent application number 0 271 983; 0 267 617; 0 261 429; 0 526 561; as an example, some of which are mentioned hereinafter.

A major drawback of this therapy however, is the limitation of the amount of drug that can be transported across the skin, in many cases, drugs which would appear to be ideal candidates for transdermal delivery are found to have such low permeability through intact skin that they cannot be delivered in therapeutically effective amounts from transdermal devices. This limitation is due to several factors. Since the skin is a protective barrier by nature, the rates of transport of most compounds through the skin is quite slow. It is generally accepted that a surface of patch beyond 50-100 sqcm would result in difficulty of application. Therefore the application of a transdermal semisolid dosage form such as a gel, cream, ointment, liquid, etc., augments the patient's compliance and the surface of application can be extended.

In order to increase skin permeability so that drugs can be delivered in therapeutically effective amounts at therapeutically effective rates, it has been proposed different systems or devices or mechanisms one of which is deliver the drug(s) in presence of permeation enhancers. Usually, using penetration enhancing compounds, processes or devices to increase drug penetration solve this problem.

Various systems were suggested for this purpose, as described in different patents such as U.S. Pat. Nos. 5,785, 991; 4,764,381; 4,956,171; 4,863,970; 5,453,279; 4,883,660; 5,719,197 or W.O. patents number 97/29735; 98/17316 or in the literature "Pharmaceutical Skin Penetration Enhancement", J. Hadgraft, Marcel Dekker, Inc. 1993; "Tercutaneous Absorption", R. Bronaugh, H. Maibach, Marcel Dekker, Inc. 1989, etc.

To be accepted, a permeation enhancer or a combination thereof should have the ability to enhance the permeability of the skin for the drug, should be non-toxic, non-irritant and non-sensitizing on repeated exposure.

It is often difficult to predict which compounds will work as permeation enhancers and which permeation enhancers will work for particular drugs. In transdermal drug delivery applications, a compound that enhances the permeability of one drug or a family of drugs may not necessarily enhance the permeability of another drug or family of drugs. That is also concluded after careful analysis of the scientific literature relating to this specific topics, such as "Transdermal Therapeutic Systemic Medications, Marcel Dekker Inc., New York, 1989" (see table on page 3).

Therefore, the usefulness of a particular compound(s) or mixture thereof as a permeation enhancer must be carefully analyzed and demonstrated by empirical work.

EPA 0 279 977 describes a transdermal device for administering progesterone and an estradiol ester alone or in combination, utilizing a polymer matrix which has the drug(s) with a penetration enhancer such as sucrose monococoate, glycerol monooleate, sucrose monolaurate, glycerol monolaureate, etc.

EPA 0 367 431 discloses that aliphatic alcohols such as isopropyl alcohol and isobutyl alcohol that are commonly used in topical transdermal formulation, thus, enhance the rate of transdermal delivery of steroid drugs.

WO 90/11 064 discloses a skin penetration enhancer composition. for transdermally administered pharmacologically active agents. The composition contains diethylene glycol monoethyl or monomethyl ether in addition to an ester component such as propylene glycol monolaurate, methyl laurate or the like.

U.S. Pat. No. 5,785,991 discloses a composition, device and method for transdermal administration of an active agent using a novel dual permeation enhancer mixture comprising lauryl acetate and a monoglyceride, glycerol monolaurate.

U.S. Pat. No. 4,764,381 discloses pharmaceutical preparations comprised of a pharmaceutically active ingredient and a carrier which comprises a percutaneous penetration enhancer comprised of 2-ethyl-1,3 hexanediol alone or in combination with oleic acid.

U.S. Pat. No. 4,863,970 discloses penetration-enhancing pharmaceutical compositions for topical transepidermal and percutaneous application which are non-irritating to the skin and describes a binary system of oleic acid or alcohol and a lower alcohol.

U.S. Pat. No. 5,453,279 describes an enhancing transdermal absorption composition useful in transdermal absorption of progestins including progesterone and optionally an estrogen for contraceptive or HRT. The enhancing composition comprise a combination of a lower alkyl ester of a polycarboxylic acid, an aliphatic monohydroxy alcohol and an aliphatic diol.

EP 0 526 561 B1 relates to the use of chemical penetration enhancers to enhance the transdermal delivery of medicaments through the skin, said chemical enhancers are alcohols.

None of the above mentioned inventions or publications report a study of lauryl alcohol together with diethylene glycol monoethyl ether in a ternary vehicle composite in a semi-solid dosage form, designed to administer transdermally or through the mucosal membrane the group of active agents mentioned in the present invention. None of the above mentioned inventions or publications describe an adequate transdermal or transmucosal formulation to deliver therapeutic plasma levels of different types of active compounds, as it is disclosed in the present invention.

One object of the present invention is to obtain a transdermal formulation that could deliver, at controlled rates, an active compound or a mixture thereof, combined with appropriate permeation enhancers. As it is well described in the literature of the art, there is not obviousness regarding the use of penetration enhancers to administer a drug(s) by transdermal route. As it is mentioned by W. R. Pfister in its chapter on "Transdermal and Dermal Therapeutic Systems: Current Status" in "Transdermal and Topical Drug Delivery Systems", Interpharm Press Inc., Buffalo Grove Ill., 1997, pages 33-112, no general guidelines exist that will ensure success in selecting an appropriate enhancer for a specific drug to be delivered from a transdermal device (Hsieh 1994). The science of optimizing topical formulations is not predictive from one drug to another and permeation enhancers can produce a wide range of enhancement factors across drugs having different physicochemical properties. Rather, this is a process that requires extensive experimental work.

It is also important to mention that transdermal permeability is mainly influenced by both physicochemical properties of the permeants and by the interaction of the permeants with the enhancers. Therefore a given enhancer could prove to be very adequate for a drug and simultaneously would not increase the permeability of the other compound. This is well illustrated by Chien, in its chapter on "Developmental Concepts and Practice in Transdermal Therapeutic Systems" in Transdermal Controlled Systemic Medications, Marcel Dekker Inc., New York, 1987, pages 25-81, who states that a penetration enhancer increases the permeation of different compound to different degree.

There has not been known an enhancer or combination thereof which shows the transdermal penetration enhancement effect for any active agent or drug. As an example we can quote results of this author as wherein below indicated:

| Drugs | Enhancement of skin permeability of various drugs by different types of enhancers | | | |
|---|---|---|---|---|
| | Enhancement factor (a) | | | |
| | Propyl myristate | Propyl oleate | Azone | Decymethyl sulfoxide |
| Progesterone | 4.56 | 5.36 | 5.96 | 11.04 |
| Estradiol | 9.33 | 14.62 | 20.17 | 12.59 |
| Hydrocortisone | 4.57 | 5.01 | 61.3 | 25.23 |
| Indomethacin | 3.77 | 4.67 | 14.49 | 15.67 |

(a) Enhancement factor = (Normalized skin permeation rate) with enhancer/ (Normalized skin permeation rate) without enhancer Additionally, another argument in favor of our position is sustained when the results reported by Chien are analyzed. He published the dependence of the enhancement factor for the skin permeation of progesterone on the alkyl chain length of saturated fatty acid in "Transdermal Controlled Systemic Medications". He found the major enhancement effect using caproic acid (C8), however the same author discloses in U.S. Pat. No. 5,145,682 that the better enhancer for estradiol is decanoic acid (C10). These results lead us to attain the same conclusion of Chien in "Transdermal Controlled Systemic Medications", Marcel Dekker, New York 1987, pages 25-81, that concludes that the efficacy of skin penetration enhancer for a specific active agent, is function of the type, concentration and, how the penetration enhancer release from the devices.

The prior art presented herein clearly prove that at least for some compounds, as shown in the present patent application, there is no such an universal penetration enhancer composition and the adequate permeation rate across the skin can be achieved only by testing different types of compounds at different concentrations. Although prior art was useful for the theoretical approach, the results herein disclosed emerged from the careful investigation of multiple variables.

BRIEF DESCRIPTION OF THE FIGURES

FIG. 20 represents Graphic XIX relevant to the data from Table XXVI for

Alprazolam pill and from Table XXVII for Alprazolam gel

Figure 21:
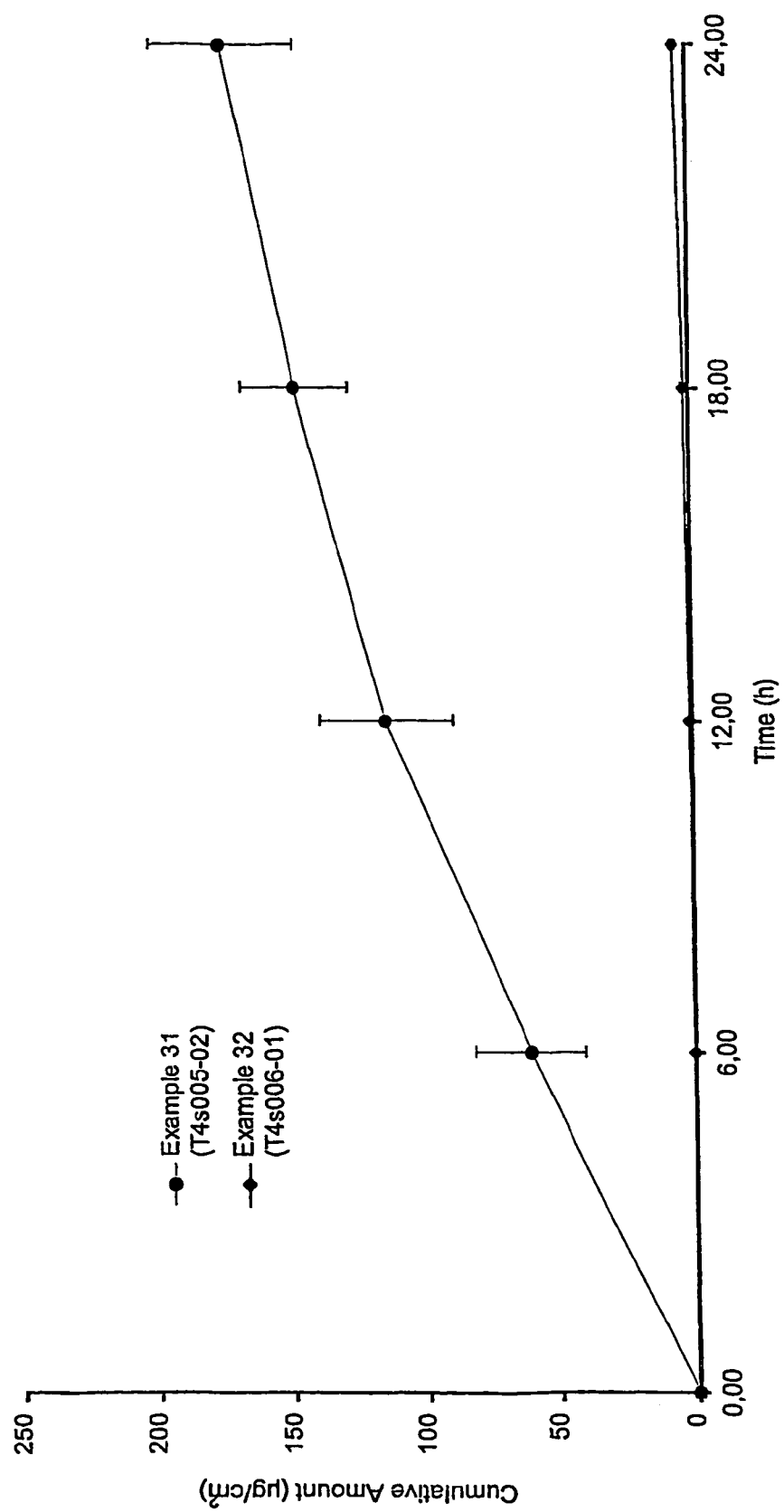

FIG. 21 represents Graphic XX relevant to the data from Table XXIX

Figure 22:
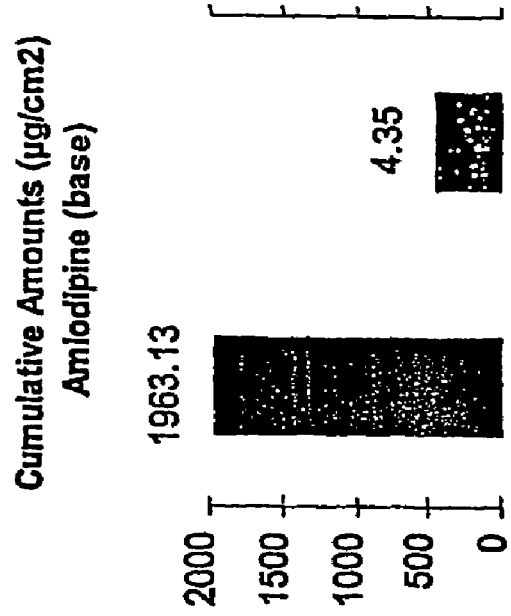

FIG. 22 represents Graphic XXII relevant to the data from Table XXX, Examples 37 and 39

Figure 23:
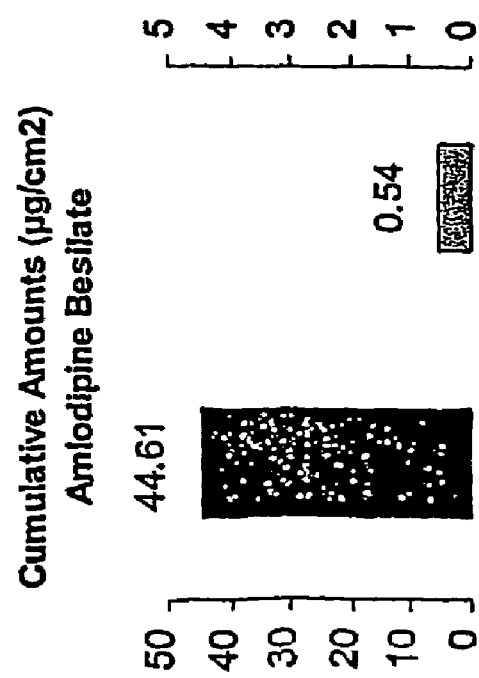

FIG. 23 represents Graphic XXI relevant to the data from Table XXX, Examples 36 and 38

SUMMARY OF THE INVENTION

The composition of the present invention relates to a penetration enhancing system that can be utilized in many types of products for topical or transdermal application, that include, but are not limited to, solutions, creams, lotions, sprays, ointment, gels, aerosols and patch devices.

While it is known in the art to combine permeation enhancers, this invention utilizes a novel combination of fatty alcohol (lauryl alcohol) and diethylene glycol monoalkyl ether (diethylene glycol monoethyl ether), and the combined effect is a significant and surprising improvement over use of lauryl alcohol or diethylene glycol monoethyl ether alone.

The present invention relates to a composition for topical application having penetration-enhancing properties, the composition comprising an active or a mixture thereof; and a penetration enhancing system that comprises lauryl alcohol and preferably also diethylene glycol monoalkyl ether in combination with a complex ternary vehicle comprising purified water, a $C_1$-$C_4$ alcohol and a glycol. The composition further comprises a gelling agent and a neutralizing agent when necessary. In preferred embodiments, the gelling agent is a carbomer (Carbopol®) which is a polyacrylic acid and/or a polyoxyethylene polyoxypropylene copolymer and the neutralizing agent is an amine like triethanolamine or tromethamine. Preservatives, flavor agents, saborizants, sweeteners any other solubilizants can be added as well.

The enhancing composition herein presented has proven to effectively enhance delivery and absorption of physiologically active substances through the skin and mucosa. That was properly demonstrated by first carrying out in vitro studies to evaluate its applicability to a determined active drug(s) and then to further confirm. its effectiveness in in vivo studies in human volunteers. The penetration enhancing system of the present invention can also be used for mucosal delivery.

Hence, it has been surprisingly discovered that it is possible to achieve a therapeutically effective, sustained and controlled penetration rate of diverse active substances into the skin with the aid of the inventive means.

It has been discovered surprisingly that the formulation discloses herein, exerts higher permeation rate when is compared with a formulation without containing the invention.

It has been surprisingly discovered also that by utilizing lauryl alcohol and diethylene glycol monoethyl ether (Transcutol®P) as enhancing composition for the invention herein disclosed, an adequate penetration enhancement factor and a sustained flux of the active agent is attained, thereafter reflected in achieving therapeutic effective, controlled and sustained levels of the active drugs by only once-a-day application of the formulation.

In another aspect, the present invention relates to a method for administering topically or systemically different active substance(s).

DETAILED DESCRIPTION OF THE INVENTION

It is often difficult to predict which compounds will work as permeation enhancers and which permeation enhancers will work for particular drugs. In transdermal drug delivery applications, a compound that enhances the permeability of one drug or a family of drugs may not necessarily enhance the permeability of another drug or family of drugs.

Therefore, the usefulness of a particular compound(s) or mixture thereof as a permeation enhancer must be carefully analyzed.

An objective of this invention is to provide a formulation, which shows adequate transdermal penetration enhancement effect for different therapeutical compounds classified in different groups.

The main objective of this invention is to provide a semisolid dosage form, which shows adequate and effective transdermal penetration enhancement for different active drugs.

Accordingly, it is an object of the present invention to provide a skin permeation enhancer composition comprising of a first component that is a saturated fatty alcohol or fatty acid given by the formula $CH_3-(CH_2)_n-CH_2OH$ or $CH_3-(CH_2)_n-CH_2COOH$ respectively, in which n is an integer from 8 to 22, preferably 8 to 12, most preferably 10 or an unsaturated fatty alcohol or fatty acid given by the formula $CH_3-(C_nH_{2(n-x)})-OH$ or $CH_3-(C_nH_{2(n-x)})-COOH$ respectively in which n is an integer from 8 to 22; and preferably also a second component that is a monoalkyl ether of diethylene glycol, preferably diethylene glycol monoethyl ether or diethylene glycol monomethyl ether, in a vehicle or carrier composition, integrated by an $Cl_1$-$C_4$ alkanol, preferably ethanol; a polyalcohol, preferably propylene glycol and purified water. The composition may also comprise additional components such as gelling agents, pH regulators, preservatives, flavor agents, saborizants, sweeteners, stabilizers, antioxidants, other solubilizants and the like.

The transdermal delivery system of the present invention comprises:

1.One or more active agents, (or a mixture thereof. The term "drug" or "active drug" or "active agents" or "pharmaceutical active drug" as used to describe the principal active ingredient of the device intends a biologically active compound or mixture compounds that has a therapeutic, prophylactic or other beneficial pharmacological and/or physiological effect on the wearer of the device. Examples of types of drugs are:

a) Hormones: estrogens such as 17 beta-Estradiol, Estradiol, Estradiol Benzoate, Estradiol 17 beta-Cypionate, Estriol, Estrone, Ethynil Estradiol, Mestranol, Moxestrol, Mytatrienediol, Polyestradiol Phosphate, Quinestradiol, Quinestrol, etc; progestogens such as Allylestrenol, Anagestone, Chlormadinone Acetate, Delmadinone Acetate, Demegestone, Desogestrel, Dimethisterone, Dydrogesterone, Ethynilestrenol, Ethisterone, Ethynodiol, Ethynodiol Diacetate, Flurogestone Acetate, Gestodene, Gestonorone Caproate, Haloprogesterone, 17-Hydroxy-16-methylene-progesterone, 17 alpha-Hydroxyprogesterone, 17 alpha-Hydroxygesterone Caproate, Lynestrenol, Medrogestone, Medroxyprogesterone, Megestrol Acetate, Melengestrol, Norethindrone, Norethindrone Acetate, Norethynodrel, Norgesterone, Norgestimate, Norgestrel, Norgestrienone, 19-Norprogesterone, Norvinisterone, Pentagestrone, Progesterone, Natural Progesterone, Promegestone, Quingestrone, Trengestone, etc; androgens such as Fluoxymesterone, Testosterone, Testosterone derivatives such as: 17-Methyltestosterone, Testosterone 17 beta-Cypionate, Testosterone Enanthate, Testosterone Nicotinate, Testosterone Pheynylacetate, Testosterone Propionate, etc.

b) Sedatives and anxyolitics for instance Benzodiazepine derivatives such as Alprazolam, Bromazepam, Flutazolam, Ketazolam, Lorazepam, Prazepam, etc; Amides such as Butoctamide, Diethylbromoacetamide, Ibrotamide, Isovaleryl Diethylamide, Niaprazine, Tricetamide, Trimetozine, Zolpidem, Zopiclone, etc; Arylpiperazines such as Buspirone, etc.

c) Antihypothyrbids such as Levothyroxine, Thyroid, Thyroxine, etc.

d) Antihypertensives for instance Benzothiadiazixie Derivatives such as Captopril, Cilazapril, Enalapril, Lisinopril, Perindopril, Ramipril; Guanidine Derivatives such as, Guanethidine; Quinazoline Derivatives such as Alfuzosin; Reserpinie Derivatives such as Reserpine, Sulfonamide Derivatives such as Furosemide; others such as Minoxidil, Amlodipine, Doxazosin Mesylate, Felodipine, Moxonidine, Nicardipine Hydrochloride, Nifedipine, Prazosin hydrochloride, etc and Calcium Channel Blockers such as Arylalkylamines such as Bepridil, Ditiazem, Fendiline, Gallopamil, Terodiline, Verapamil; Dihydropyridine Derivatives such as Felodipine, Isradipine, Nicardipine, Nifedipine, Nilvadipine, Nimodipine, Nisoldipine, Nitrendipine, Piperazine; Derivatives such as Flunarisine; others such as Perhexiline Calcium Regulator such as Calcifediol, Calcitonin, Calcitriol, Clodronic Acid, Dihydrotachysterol, Elcatonin, Etidronic Acid, Ipriflavone, Pamidronic Acid, Parathyroid Hormone, Teriparatide Acetate, etc.

The present invention could be applied to other groups of pharmaceutical active agents for instance for alpha-Adrenergic Agonists such as Budralazine, Clonidine, Epinephrine, Fenoxazoline, Naphazoline, Phenylephrine, Phenylpropanolamine, beta-Adrenergic Agonists such as Formoterol, Methoxyphenamine, alpha-Adrenergic Blockers such as Doxazosin, Prazosin, Terazosin, Trimazosin, Yohimbine, beta-Adrenergic Blockers such as Atenolol, Bisoprolol, Carteolol, Carvedilol, Metoprolol, Nadolol, Penbutolol, Analgesics (Narcotics) such as Buprenorphine, Dihydromorphine, Metazocine, Methadone, Morphine, Morphine Derivatives, Nicomorphine, Oxymorphone, etc.; Nerve Agents for smoking cessation i.e. such as Nicotine, Nicotine Citrate and Nicotine Tartrate, Antineoplastic Agents such as 5-Fluorouracil, etc; Analgesics (Non-Narcotics), Analgesic and Anti-Inflamatory Agents; Anesthetics; Antiandrogens; Antianginals; Anticholinergics; Anticonvulsants; Antidepressants; Antiepileptics; Antiestrogen such as Tamoxifen, 4-OH Tamoxifen; Antihistaminics; Antiparkinsonians; Bronchodilators; Diuretics; Glucocorticoids; Muscle Relaxants; Narcotic Antagonists; etc.

It is to be understood herein that the active agent is intended to mean a single active agent or a combination of more than one active agent.

The amount of the systemically and/or topically active agent included in the formulation is subject to the degree to which penetration enhancement is achieved.

In the preferred embodiments, the active agents are: Testosterone presented in the compositions in about 0.05 to about 10.0% w/w; preferably from about 0.1 to about 5.0% w/w and more preferably 0.6 to 4.0% w/w. Estradiol presented in the compositions in about 0.02 to about 3.0% w/w; preferably from about 0.04 to 2.0% w/w and more preferably 0.06 to 0.12% w/w. Ethynil Estradiol presented in the compositions in about 0.02 to about 3.0% w/w; preferably from about 0.04 to 0.5% w/w and more preferably 0.06 to 0.12% w/w. Levonorgestrel presented in the compositions in about 0.02 to about 3.0% w/w; preferably from about 0.04 to 0.5% w/w and more preferably 0.06 to 0.12% w/w. Progesterone presented in the compositions in about 0.1 to about 10.0% w/w; preferably from about 0.1 to 5.0% w/w and more preferably 1.0 to 3.0% w/w. Alprazolam presented in the compositions in about 0.02 to about 6.0% w/w; preferably from about 0.1 to 3.0% w/w and more preferably 0.5 to 2.0% w/w. L-Thyroxine presented in the compositions in about 0.02 to about 4.0% w/w; preferably from about 0.04 to 2.0% w/w and more preferably 0.2 to 1.0% w/w. Amlodipine or Amlodipine Besylate presented in the compositions in about 0.05 to about 5.0% w/w; preferably from about 0.2 to 3.0% w/w and more preferably 0.5 to 2.0% w/w.

2. A ternary vehicle composite comprised of a $C_2$-$C_4$ alkanol such as ethanol, isopropanol, n-propanol, butanol, preferably ethanol; a polyalcohol or glycol such as propylene glycol, butylene glycol, hexylene glycol, ethylene glycol, preferably propylene glycol and finally purified water. The compositions in accordance with the present invention contain an alcohol, preferably ethanol, in an amount of about 5.0 to about 75.0% w/w; preferably from about 15.0% to about 65.0% w/w and more preferably 20.0 to 55.0% w/w. In addition, the compositions of the present invention comprises a glycol, preferably propylene glycol in about 0.5 to about 50.0% w/w; preferably from about 3.0 to 20.0% w/w and more preferably 4.0 to 10.0% w/w.

3. A permeation enhancer system comprising of a first component that is a saturated fatty alcohol or fatty acid given by the formula $CH_3$—$(CH_2)_n$—$CH_2OH$ or $CH_3$—$(CH_2)_n$—$CH_2COOH$ respectively, in which n is an integer from 8 to 22, preferably 8 to 12, most preferably 10 or an unsaturated fatty alcohol or fatty acid given by the formula $CH_3$—$(C_nH_{2(n-x)})$—$OH$ or $CH_3$—$(C_nH_{2(n-x)})$—$COOH$ respectively in which n is an integer from 8 to 22; and preferably also a second component that is a monoalkyl ether of diethylene glycol, preferably diethylene glycol monoethyl ether or diethylene glycol monomethyl. The compositions in accordance with the present invention contain a fatty alcohol, preferably lauryl alcohol or dodecanol in about 0.1 to about 20.0% w/w on the whole composition; preferably form about 0.4 to 10.0% w/w and more preferably 0.2 to 3.0% w/w; and, optionally, a diethylene glycol monoalkyl ether in amount up to 40.0% w/w; preferably from about 0.2 to 25.0% w/w and more preferably 2.0 to 8.0% w/w.

4. A gelling agent or viscosant, e.g. carbomer, carboxyethylene or polyacrylic acid such as Carbopol 980 or 940 NF, 981 or 941 NF, 1382 or 1342 NF, 5984 or 934 NF, ETD 2020, 2050, 934P NF, 971P NF, 974P NF, Noveon AA-1 USP, etc; cellulose derivatives such as ethylcellulose, hydroxypropylmethylcellulose (HPMC), ethyl-hydroxyethylcellulose (EHEC), carboxymethylcellulose (CMC), hydroxypropylcellulose (HPC) (Klucel different grades), hydroxyethylcellulose (HEC) (Natrosol grades), HPMCP 55, Methocel grades, etc; natural gums such as arabic, xanthan, guar gums, alginates, etc; polyvinylpyrrolidone derivatives such as Kollidon grades; polyoxyethylene polyoxypropylene copolymers such as Lutrol F grades 68, 127, etc; others like chitosan, polyvinyl alcohols, pectins, veegun grades, etc. In the present invention, Lutrol F grades and carbopol grades were preferred. Those of the skill in the art should know of other gelling agents or viscosants that are suitable to practice the present invention. Suitable gelling agents to apply the present invention include, but are not limited to, Carbopol 980 NF, Lutrol F 127, Lutrol F 68 and Noveon AA-1 USP. The gelling agent is present from about 0.2 to about 30.0% w/w depending on the type of polymer.

5. A pH regulator, normally a neutralizant agent, which can optionally have crosslinking function e.g. a ternary amine such as triethanolamine, tromethamine, tetrahydroxypropylethylendiamine, etc; NaOH solution, etc. The pH regulator is present in the formulations in about 0.05 to about 2.0% w/w.

6. Other ingredients can optionally be included, for example, preservatives and/or antioxidants such as buthylhydroxytoluene, buthylhydroxyanisole, ethylenediaminetetraacetic acid and its sodium salts, DL-alfa tocoferol, antioxidant complexes, etc; co-solvents or solubilizers such as glycerol, polyethylene glycols, polyethylene glycols derivatives, polyethyleneglycol 660 hydroxystearate (Solutol HS15 from Basf), buthylene glycol, hexylene glycol, etc.

The formulations in which the present invention could be added, assume any of a variety of dosage forms. Examples are gels, creams, lotions, sprays, ointments, aerosols, patches, buccal and sublingual tablets, suppositories, vaginal dosage forms and different passive or/and active transdermal devices for absorption through the skin or mucosa.

As such, in another aspect, the present invention relates to a method for administering topically or systemically active agent(s), comprising: 1. An active agent(s); 2. A ternary vehicle composite (composed by a C1-C4 alkanol, a glycol and water); 3. A penetration enhancers combination. (fatty alcohol or acid and diethylene glycol monoethyl ether); 4. A gelling agent and 5. A pH regulator.

It has been discovered that in a transdermal formulation comprising different group of drugs as active agents; lauryl alcohol and diethylene glycol monoethyl ether as penetration enhancers, in a ternary vehicle composite comprised of ethanol, propylene glycol and purified water, using a polymer or copolymer of acrylic acid, preferably a carbomer as gelling forming, provides therapeutically effective serum concentration of each active agent throughout at least a 24 hours period. As it is concluded when a bioavailability study of the above mentioned formulations were carried out in human beings volunteers.

The main aim followed by the present invention is to rapidly create a high concentration of the drug(s) in contact with the skin or mucosa attained by the careful combination of permeation enhancers and vehicles.

It is well known by the skills in the art that a sumatory or a sinergistic effect could be expected when two or more penetration enhancers are combined and included into a formulation. However, it is by no mean obvious to obtain an adequate penetration enhancement factor and a sustained flux of the active agent(s), achieving therapeutic effective levels, also controlled and sustained, by only one daily application of the formulation.

Accordingly, we can postulate that the behavior of our formulation was due to the addition of several phenomena especially on the stratum corneum.

Although the mechanism of such stratum corneum effect in the present invention is not fully clear by the scientific knowledge up to now, it can be understood as follows:

The fatty alcohol is mainly distributed to the stratum corneum because of its lipophilicity and interacts with the stratum corneum lipids.

The diethylene glycol monoethyl ether dissolves both an hydrophilic and a lipophilic active agents therein and facilitates the penetration of the active agents to the skin.

An alkanol, such as ethanol, also has a function to increase the stratum corneum liquid fluidity or a function to extract lipids from the stratum corneum.

Propylene glycol, a widespread pharmaceutical vehicle, acts as a cosolvent of the drugs hence increase the solubility of the active agent in the formulation and solvated the intracellular keratin of the stratum corneum and thus enhanced drug mobility and skin hydration.

Water serves to augment the solubility of a hydrophilic active agent in the formulation and accelerates the release of lipophilic active agent from a formulation.

A polymer or copolymer of acrylic acid, such as a carbomrer acts as a gelling forming and facilitates the release of lipophilic active agent and penetration enhancer.

A tertiary amine, such as triethanolamine of trolamine, has the function to thicken and neutralize the system.

In the preferred embodiment of the present invention, the active agents and the compounds which enhances their penetration rate (lauryl alcohol and diethylene glycol monoethyl ether) are dissolved in a ternary vehicle composite integrated by an alkanol having 1-4 C atoms, preferably ethanol; a polyalcohol, preferably propylene glycol and purified water.

This invention relates to a novel composition for transdermal or transmucosal application to humans in an optimized dosage form and methods for providing therefrom a controlled and sustained administration of different group of drugs.

It is an object of the present invention to demonstrate its applicability not only for hormones but also for different group of pharmaceutical active agents.

Definition of Terms

"Penetration enhancement" or "permeation enhancement" as used herein relates to an increase in the permeability of skin to a pharmacologically active agent, i.e., so as to increase the rate at which the drug permeates through the skin and enters the bloodstream. The enhanced permeation effected through the use of such enhancers, and in particular, through the use of the enhancer composition of the present invention, can be observed by measuring the rate of diffusion of drug through animal or human skin using a diffusion cell apparatus as described in the examples herein.

An "effective" or an "adequate" permeation enhancer as used herein means a permeation enhancer that will provide the desired increase in skin permeability and correspondingly, the desired depth of penetration, rate of administration, and amount of drug delivered.

By "transdermal" delivery, applicants intend to include both transdermal (or "percutaneous") and transmucosal administration, i.e., delivery by passage of a drug through the skin or mucosal tissue and into the bloodstream.

"Carriers" or "vehicles" as used herein refer to carrier materials suitable for transdermal drug administration, and include any such materials known in the art, e.g., any liquid, gel, solvent, liquid diluent, solubilizer, or the like, which is non toxic and which does not interact with other components of the composition in a deleterious manner. Examples of suitable vehicles for use herein include water, alcohols, polyalcohols, and glycols.

By the term "pharmacologically active agent" or "drug" as used herein is meant any chemical material or compound suitable for transdermal or transmucosal administration which induces a desired systemic effect.

By "controlled" is meant reduce or minimize peak and valley normally present in some routes of administration of a pharmacologically active agent.

By "sustained" is meant extended maintenance of steady state plasma levels.

By "therapeutically effective" amount of a pharmacologically active agent is meant sufficient amount of a compound to provide the desired therapeutic effect, avoiding high or low plasmatic levels, obtaining, therefore, plasmatic levels of active within the therapeutic window.

EXAMPLES

In order to further illustrate the present invention and the advantages thereof, the following specific examples are given. It being understood that the examples herein disclosed are intended only as illustrative and in nowise limitative.

All the examples were prepared basically as follow: an aqueous phase (dispersion of the carbomer in water) and an alcoholic phase (solution containing the active drugs, Lauryl Alcohol, Diethylene glycol monoethyl ether (Transcutol P), and Ethyl Alcohol, or some of them according to the formulation), were prepared separately. The Propylene Glycol and Disodium EDTA, were added to the aqueous phase after the carbomer dispersion. Finally, aqueous and alcoholic phases were mixed and Triethanolanine was added to neutralize the carbomer and form the gel. The exemption was gels containing Hydroxypropyl Cellulose, which were manufactured by dispersing the Hydroxypropyl Cellulose in the hydroalcoholic solution containing the rest of the components.

The solutions were prepared by dissolving the active drugs in the rest of the excipients and shaking up to total dissolution.

The active substances included in the different formulations used in the examples or referred to in tables and graphics are defined through the following list of initials:
LNEg=Levonorgestrel+Estradiol gel
Tg=Testosterone gel
NEg=Norethindrone Acetate+Estradiol gel
Pg=Progesterone gel
EELNg=Ethynil Estradiol+Levonorgestrel gel
Alg=Alprazolam gel
T4s=L-Thyroxine solution
T4g=L-Thyroxine gel
Alps=Alprazolam solution
TEg=Testosterone+Estradiol gel
Ams=Amlodipine solution
AmBss=Amlodipine Besylate solution Then, a numbering that represents different formulations with the same active drug (s) and same dosage form follows the initials.

Example 1 (Tg017-04)

A gel composed by Testosterone 1.25% w/w, Lauryl Alcohol 2.00% w/w, Diethylene glycol monoethyl ether (Transcutol P) 4.99% w/w, Propylene Glycol 6.00% w/w, Ethyl Alcohol 42.10% w/w, Distilled Water 42.01% w/w, Carbomer (Carbopol 980 NF) 1.21% w/w, Triethanolamine 0.38% w/w, Disodium EDTA 0.06% w/w was prepared according to the manufacturing technique herein described.

Example 2 (Tg028-01)

A gel composed by Testosterone 1.25% w/w, Diethylene glycol monoethyl ether (Transcutol P) 5.00% w/w, Propylene Glycol 5.95% w/w, Ethyl Alcohol 43.09% w/w, Distilled Water 43.07% w/w, Carbomer (Carbopol 980 NF) 1.20% w/w, Triethanolamine 0.38% w/w, Disodium EDTA 0.059% w/w was prepared according to the manufacturing technique herein described.

Example 3 (TR029-01)

A gel composed by Testosterone 1.25% w/w, Lauryl Alcohol 2.01% w/w, Propylene Glycol 6.05% w/w, Ethyl Alcohol 44.53% w/w, Distilled Water 44.58% w/w, Carbomer (Carbopol 980 NF) 1.23% w/w, Triethanolamine 0.38% w/w, Disodium EDTA 0.060% w/w was prepared according to the manufacturing technique herein described.

Example 4 (Tg014-01)

A gel composed by Testosterone 2.50% w/w, Lauryl Alcohol 2.02% w/w, Diethylene glycol monoethyl ether (Transcutol) 5.00% w/w, Propylene Glycol 6.02% w/w, Ethyl Alcohol 45.57% w/w, Distilled Water 37.29% w/w, Carbomer (Carbopol 980 NF) 1.20% w/w, Triethanolamine 0.35% w/w, Disodium EDTA 0.06% w/w was prepared according to the manufacturing technique herein described.

Example 5 (Tg018-01)

A gel composed by Testosterone 3.50% w/w, Lauryl Alcohol 2.00% w/w, Diethylene glycol monoethyl ether (Transcutol) 5.01% w/w, Propylene Glycol 5.93% w/w, Ethyl Alcohol 49.22% w/w, Distilled Water 32.73% w/w, Carbomer -(Carbopol 980 NF) 1.20% w/w, Triethanolamine 0.35% w/w, Disodium EDTA 0.06% w/w was prepared according to the manufacturing technique herein described.

Example 6 (Tg019-01)

A gel composed by Testosterone 0.60% w/w, Lauryl Alcohol 2.00% w/w, Diethylene glycol monoethyl ether (Transcutol) 5.02% w/w, Propylene Glycol 5.94% w/w, Ethyl Alcohol 42.41% w/w, Distilled Water 42.41% w/w, Carbomer (Carbopol 980 NF) 1.20% w/w, Triethanolamine 0.36% w/w, Disodium EDTA 0.06% w/w was prepared according to the manufacturing technique herein described.

Example 7 (Tg020-01)

A gel composed by Testosterone 0.30% w/w, Lauryl Alcohol 2.00% w/w, Diethylene glycol monoethyl ether (Transcutol) 4.96% w/w, Propylene Glycol 5.95% w/w, Ethyl Alcohol 42.64% w/w, Distilled Water 42.52% w/w, Carbomer (Carbopol 980 NF) 1.20% w/w, Triethanolamine 0.36% w/w, Disodium EDTA 0.06% w/w was prepared according to the manufacturing technique herein described.

Example 8 (Tg021-01)

A gel composed by Testosterone 1.25% w/w, Lauryl Alcohol 2.11% w/w, Diethylene glycol monoethyl ether (Transcutol) 5.07% w/w, Propylene Glycol 6.01% w/w, Ethyl Alcohol 46.19% w/w, Distilled Water 37.78% w/w, Carbomer (Carbopol 980 NF) 1.20% w/w, Triethanolamine 0.33% w/w, Disodium EDTA 0.06% w/w was prepared according to the manufacturing technique herein described.

Example 9 (Tg030-01)

A gel composed by Testosterone 1.25% w/w, Propylene Glycol 5.95% w/w, Ethyl Alcohol 45.46% w/w, Distilled Water 45.67% w/w, Carbomer (Carbopol 980 NF) 1.21% w/w, Triethanolamine 0.39% w/w, Disodium EDTA 0.06% w/w was prepared according to the manufacturing technique herein described.

Example 10 (Tg035-02)

A gel composed by Testosterone 1.25% w/w, Lauryl Alcohol 2.02% w/w, Diethylene glycol monoethyl ether (Transcutol P) 5.01% w/w, Propylene Glycol 6.00% w/w, Ethyl Alcohol 46.25% w/w, Distilled Water 37.91% w/w, Carbomer (Carbopol 980 NF) 1.21% w/w, Triethanolamine 0.35% w/w was prepared according to the manufacturing technique herein described.

Example 11 (Tg036-01)

A gel composed by Testosterone 2.50% w/w, Lauryl Alcohol 2.00% w/w, Diethylene glycol monoethyl ether (Transcutol P) 5.00% w/w, Propylene Glycol 6.00% w/w, Ethyl Alcohol 47.27% w/w, Distilled Water 35.67% w/w, Carbomer (Carbopol 980 NF) 1.20% w/w, Triethanolamine 0.35% w/w was prepared according to the manufacturing technique herein described.

Example 12 (Tg037-01)

A gel composed by Testosterone 1.25% w/w, Lauryl Alcohol 2.00% w/w, Propylene Glycol 5.99% w/w, Ethyl Alcohol 49.00% w/w, Distilled Water 40.19% w/w, Carbomer (Carbopol 980 NF) 1.21% w/w, Triethanolamine 0.35% w/w was prepared according to the manufacturing technique herein described.

Example 13 (Tg038-01)

A gel composed by Testosterone 1.25% w/w, Lauryl Alcohol 1.99% w/w, Oleyl alcohol 1.50% w/w, Diethylene glycol monoethyl ether (Transcutol P) 5.00% w/w, Propylene Glycol 6.02% w/w, Ethyl Alcohol 45.42% w/w, Distilled Water 37.23% w/w, Carbomer (Carbopol 980 NP) 1.20% w/w, Triethanolamine 0.36% w/w was prepared according to the manufacturing technique herein described.

Example 14 (Tg039-01)

A gel composed by Testosterone 1.25% w/w, Lauryl Alcohol 1.01% w/w, Diethylene glycol monoethyl ether (Transcutol P) 5.01% w/w, Propylene Glycol 6.00% w/w, Ethyl Alcohol 44.24% w/w, Distilled Water 40.93% w/w, Carbomer (Carbopol 980 NF) 1.21% w/w, Triethanolamine 0.35% w/w was prepared according to the manufacturing technique herein described.

Example 15 (Tg040-01)

A gel composed by Testosterone 2.50% w/w, Lauryl Alcohol 1.00% w/w, Diethylene glycol monoethyl ether (Transcutol P) 5.02% w/w, Propylene Glycol 5.99% w/w, Ethyl Alcohol 46.02% w/w, Distilled Water 37.92% w/w, Carbomer (Carbopol 980 NF) 1.20% w/w, Triethanolamine 0.35% w/w was prepared according to the manufacturing technique herein described.

Example 16 (TEg002-01)

A gel composed by Testosterone 0.183% w/w, 17β-Estradiol 0.060% w/w, Lauryl Alcohol 1.99% w/w, Diethylene glycol monoethyl ether (Transcutol) 5.10% w/w, Propylene Glycol 6.09% w/w, Ethyl Alcohol 45.00% w/w, Distilled Water 39.96% w/w, Carbomer (Carbopol 980 NF) 1.21% w/w, Triethanolamine 0.35% w/w, Disodium EDTA 0.06% w/w was prepared according to the manufacturing technique herein described.

Example 17 (TEg005-01)

A gel composed by Testosterone 0.60% w/w, 17β-Estradiol 0.062% w/w, Lauryl Alcohol 2.01% w/w, Diethylene glycol monoethyl ether (Transcutol) 5.13% w/w, Propylene Glycol 5.99% w/w, Ethyl Alcohol 46.54% w/w, Distilled Water 38.08% w/w, Carbomer (Carbopol 980 NF) 1.20% w/w, Triethanolamine 0.34% w/w, Disodium EDTA 0.06% w/w was prepared according to the manufacturing technique herein described.

Example 18 (TEg006-01)

A gel composed by Testosterone 0.20% w/w, 17β-Estradiol 0.06% w/w, Lauryl Alcohol 2.00% w/w, Diethylene glycol monoethyl ether (Transcutol) 5.00% w/w, Propylene Glycol 5.99% w/w, Ethyl Alcohol 45.11% w/w, Distilled Water 40.03% w/w, Carbomer (Carbopol 980 NF) 1.20% w/w, Triethanolamine 0.35% w/w, Disodium EDTA 0.06% w/w was prepared according to the manufacturing technique herein described.

Example 19 (TEg008-01)

A gel composed by Testosterone 0.10% w/w, 17β-Estradiol 0.06% w/w, Lauryl Alcohol 2.00% w/w, Diethylene glycol monoethyl ether (Transcutol) 5.00% w/w, Propylene Glycol 6.00% w/w, Ethyl Alcohol 45.16% w/w, Distilled Water 40.07% w/w, Carbomer (Carbopol 980 NF) 1.20% w/w, Triethanolamine 0.35% w/w, Disodium EDTA 0.06% w/w was prepared according to the manufacturing technique herein described.

Example 20 (TEg009-01)

A gel composed by Testosterone 0.06% w/w, 17β-Estradiol 0.058% w/w, Lauryl Alcohol 2.00% w/w, Diethylene glycol monoethyl ether (Transcutol P) 5.00% w/w, Propylene Glycol 6.00% w/w, Ethyl Alcohol 45.18% w/w, Distilled Water 40.09% w/w, Carbomer (Carbopol 980 NF) 1.20% w/w, Triethanolamine 0.35% w/w, Disodium EDTA 0.06% w/w was prepared according to the manufacturing technique herein described.

Example 21 (EELNg001-01)

A gel composed by Ethynil Estradiol 0.060% w/w, Levonorgestrel 0.089% w/w, Lauryl Alcohol 1.99% w/w, Diethylene glycol monoethyl ether (Transcutol) 4.98% w/w, Propylene Glycol 6.13% w/w, Ethyl Alcohol 45.20% w/w, Distilled Water 39.94% w/w, Carbomer (Carbopol 980 NF) 1.21% w/w, Triethanolamine 0.34% w/w, Disodium EDTA 0.06% w/w was prepared according to the manufacturing technique herein described.

Example 22 (EELNg002-01)

A gel composed by Ethynil Estradiol 0.090% w/w, Levonorgestrel 0.090% w/w, Lauryl Alcohol 2.02% w/w, Diethylene glycol monoethyl ether (Transcutol) 5.00% w/w, Propylene Glycol 6.00% w/w, Ethyl Alcohol 45.13% w/w, Distilled Water 40.06% w/w, Carbomer (Carbopol 980 NF)

1.20% w/w, Triethanolamine 0.34% w/w, Disodium EDTA 0.06% w/w was prepared according to the manufacturing technique herein described.

Example 23 (Alg004-02)

A gel composed by Alprazolam 1.00% w/w, Lauryl Alcohol 2.08% w/w, Diethylene glycol monoethyl ether (Transcutol) 5.01% w/w, Propylene Glycol 6.12% w/w, Ethyl Alcohol 44.65% w/w, Distilled Water 39.58% w/w, Carbomer (Carbopol 980 NF) 1.20% w/w, Triethanolamine 0.36% w/w was prepared according to the manufacturing technique herein described.

Example 24 (Alg005-01)

A gel composed by Alprazolam 1.80% w/w, Lauryl Alcohol 1.99% w/w, Diethylene glycol monoethyl ether (Transcutol) 5.00% w/w, Propylene Glycol 6.11% w/w, Ethyl Alcohol 44.32% w/w, Distilled Water 39.25% w/w, Carbomer (Carbopol 980 NF) 1.20% w/w, Triethanolamine 0.34% w/w was prepared according to the manufacturing technique herein described.

Example 25 (Alg006-01)

A gel composed by Alprazolam 1.00% w/w, Oleic Acid 1.01% w/w, Diethylene glycol monoethyl ether (Transcutol) 5.00% w/w, Propylene Glycol 5.99% w/w, Ethyl Alcohol 45.30% w/w, Distilled Water 40.09% w/w, Carbomer (Carbopol 980 NF) 1.26% w/w, Triethanolamine 0.35% w/w was prepared according to the manufacturing technique herein described.

Example 26 (Alg007-01)

A gel composed by Alprazolam 1.80% w/w, Lauryl Alcohol 2.03% w/w, Diethylene glycol monoethyl ether (Transcutol) 5.03% w/w, Propylene Glycol 6.00% w/w, Ethyl Alcohol 46.81% w/w, Distilled Water 36.77% w/w, Carbomer (Carbopol 980 NF) 1.21% w/w, Triethanolamine 0.36% w/w was prepared according to the manufacturing technique herein described.

Example 27 (Alg008-01)

A gel composed by Alprazolam 0.50% w/w, Lauryl Alcohol 1.99% w/w, Diethylene glycol monoethyl ether (Transcutol P) 21.94% w/w, Propylene Glycol 11.04% w/w, Solutol 11.01% w/w, Lutrol F127 7.00% w/w, Lutrol F68 3.00% w/w, Distilled Water 42.23% w/w, Noveon AA-1 1.01% w/w, Triethanolamine 0.30% w/w was prepared according to the manufacturing technique herein described.

Example 28 (Alg009-01)

A gel composed by Alprazolam 0.50% w/w, Lauryl Alcohol 2.01% w/w, Diethylene glycol monoethyl ether (Transcutol P) 13.52% w/w, Propylene Glycol 13.52% w/w, Lutrol F127 6.99% w/w, Lutrol F68 3.00% w/w, Ethyl Alcohol 25.13% w/w, Distilled Water 33.97% w/w, Noveon AA-1 1.01% w/w, Triethanolamine 0.30% w/w was prepared according to the manufacturing technique herein described.

Example 29 (Alg010-01)

A gel composed by Alprazolam 0.50% w/w, Propylene Glycol 15.16% w/w, Lutrol F127 7.00% w/w, Lutrol F68 3.00% w/w, Solutol HS15 15.17% w/w, Distilled Water 57.90% w/w, Noveon AA-1 0.99% w/w, Triethanolamine 0.30% w/w was prepared according to the manufacturing technique herein described.

Example 30 (Alg016-01)

A gel composed by Alprazolam 1.00% w/w, Lauryl Alcohol 1.01% w/w, Diethylene glycol monoethyl ether (Transcutol P) 5.01% w/w, Propylene Glycol 6.02% w/w, Ethyl Alcohol 45.28% w/w, Distilled Water 40.13% w/w, Carbomer (Carbopol 980 NP) 1.20% w/w, Triethanolamine 0.35% w/w was prepared according to the manufacturing technique herein described.

Example 31 (T4s005-02)

A clear solution composed by Na L-Thyroxine 0,40% w/w, Lauryl Alcohol 1.97% w/w, Diethylene glycol monoethyl ether (Transcutol P) 5.03% w/w, Propylene Glycol 6.04% w/w, Ethyl Alcohol 45.92% w/w, Distilled Water 40.64% w/w was prepared.

Example 32 (T4s006-01)

A clear solution composed by Na L-Thyroxine 0.40% w/w, Propylene Glycol 5.94% w/w, Ethyl Alcohol 49.68% w/w, Distilled Water 43.98% w/w was prepared.

Example 33 (T4g005-01)

A gel composed by Na L-Thyroxine 0.41% w/w, Lauryl Alcohol 2.06% w/w, Diethylene glycol monoethyl ether (Transcutol P) 5.13% w/w, Propylene Glycol 6.10% w/w, Ethyl Alcohol 45.81% w/w, Distilled Water 38.58% w/w, Hydroxypropyl Cellulose 1.90% w/w was prepared according to the manufacturing technique herein described.

Example 34 (NEg098-05)

A gel composed by 17β-Estradiol 0.060% w/w, Norethindrone Acetate 1.20% w/w, Lauryl Alcohol 2.00% w/w, Diethylene glycol monoethyl ether (Transcutol P) 5.00% w/w, Propylene Glycol 6.00% w/w, Ethyl Alcohol 44.57% w/w, Distilled Water 39.55% w/w, Carbomer (Carbopol 980 NF) 1.21% w/w, Triethanolamine 0.35% w/w, Disodium EDTA 0.060% w/w was prepared according to the manufacturing technique herein described.

Example 35 (NEg098-06)

A gel composed by 17β-Estradiol 0.060% w/w, Norethindrone Acetate 1.20% w/w, Lauryl Alcohol 2.00% w/w, Diethylene glycol monoethyl ether (Transcutol P) 5.00% w/w, Propylene Glycol 5.97% w/w, Ethyl Alcohol 44.58% w/w, Distilled Water 39.57% w/w, Carbomer (Carbopol 980 NF) 1.20% w/w, Triethanolamine 0.35% w/w, Disodium EDTA 0.061% w/w was prepared according to the manufacturing technique herein described.

Example 36 (Ams001-01)

A solution composed by Amlodipine base 1.00% w/w, Propylene Glycol 99.00% w/w, was prepared according to the manufacturing technique herein described.

Example 37 (AmBss001-01)

A solution composed by Amlodipine Besylate 1.00% w/w, Propylene Glycol 99.00% w/w, was prepared according to the manufacturing technique herein described.

Example 38 (Ams002-01)

A solution composed by Amlodipine base 1.00% w/w, Lauryl Alcohol 2.06% w/w, Diethylene glycol monoethyl ether (Transcutol P) 5.15% w/w, Propylene Glycol 91.79% w/w, was prepared according to the manufacturing technique herein described.

Example 39 (AmBss002-01)

A solution composed by Amlodipine Besylate 1.00% w/w, Lauryl Alcohol 2.07% w/w, Diethylene glycol monoethyl ether (Transcutol P) 5.15% w/w, Propylene Glycol 91.78% w/w, was prepared according to the manufacturing technique herein described.

Example 40 (Pg001-01)

A gel composed by Progesterone 1.00% w/w, Lauryl Alcohol 2.00% w/w, Diethylene glycol monoethyl ether (Transcutol P) 5.02% w/w, Propylene Glycol 6.01% w/w, Ethyl Alcohol 44.78% w/w, Distilled Water 39.77% w/w, Carbomer (Carbopol 980 NF) 1.21% w/w, Triethanolamine 0.38% w/w, was prepared according to the manufacturing technique herein described.

Example 41 (Pg002-01)

A gel composed by Progesterone 2.00% w/w, Lauryl Alcohol 2.01% w/w, Diethylene glycol monoethyl ether (Transcutol P) 5.00% w/w, Propylene Glycol 6.02% w/w, Ethyl Alcohol 44.18% w/w, Distilled Water 39.21% w/w, Carbomer (Carbopol 980 NF) 1.20% w/w, Triethanolamine 0.39% w/w, was prepared according to the manufacturing technique herein described.

Example 42 (LNEg011-01)

A gel composed by Levonorgestrel 0.05% w/w, 17β-Estradiol 0.100% w/w, Lauryl Alcohol 2.00% w/w, Diethylene glycol monoethyl ether (Transcutol P) 5.00% w/w, Propylene Glycol 6.01% w/w, Ethyl Alcohol 45.18% w/w, Distilled Water 40.05% w/w, Carbomer (Carbopol 980 NF) 1.20% w/w, Triethanolamine 0.35% w/w, Disodium EDTA 0.06% w/w was prepared according to the manufacturing technique herein described.

Example 43 (LNEg002-01)

A gel composed by Levonorgestrel 0.090% w/w, 17β-Estradiol 0.060% w/w, Lauryl Alcohol 2.00% w/w, Diethylene glycol monoethyl ether (Transcutol) 5.00% w/w, Propylene Glycol 6.00% w/w, Ethyl Alcohol 45.18% w/w, Distilled Water 40.07% w/w, Carbomer (Carbopol 980 NF) 1.20% w/w, Triethanolamine 0.35% w/w, Disodium EDTA 0.06% w/w was prepared according to the manufacturing technique herein described.

Example 44 (LNEg003-01)

A gel composed by Levonorgestrel 0.030% w/w, 17β-Estradiol 0.061% w/w, Lauryl Alcohol 2.01% w/w, Diethylene glycol monoethyl ether (Transcutol) 4.98% w/w, Propylene Glycol 5.95% w/w, Ethyl Alcohol 45.30% w/w, Distilled Water 40.03% w/w, Carbomer (Carbopol 980 NF) 1.22% w/w, Triethanolamine 0.36% w/w, Disodium EDTA 0.06% w/w was prepared according to the manufacturing technique herein described.

Example 45 (LNEg012-01)

A gel composed by Levonorgestrel 0.090% w/w, 17β-Estradiol 0.060% w/w, Lauryl Alcohol 2.02% w/w, Diethylene glycol monoethyl ether (Transcutol) 5.00% w/w, Propylene Glycol 6.01% w/w, Ethyl Alcohol 45.20% w/w, Distilled Water 40.07% w/w, Carbomer (Carbopol 980 NF) 1.20% w/w, Triethanolamine 0.35% w/w, was prepared according to the manufacturing technique herein described.

Example 46 (LNEg015-01)

A gel composed by Levonorgestrel 0.090% w/w, 17β-Estradiol 0.061% w/w, Propylene Glycol 6.03% w/w, Ethyl Alcohol 48.82% w/w, Distilled Water 43.42% w/w, Carbomer (Carbopol 980 NF) 1.20% w/w, Triethanolamine 0.36% w/w, was prepared according to the manufacturing technique herein described.

Example 47 (LNEg013-01)

A gel composed by Levonorgestrel 0.091% w/w, 17β-Estradiol 0.100% w/w, Lauryl Alcohol 2.00% w/w, Diethylene glycol monoethyl ether (Transcutol) 5.00% w/w, Propylene Glycol 6.00% w/w, Ethyl Alcohol 45.16% w/w, Distilled Water 40.07% w/w, Carbomer (Carbopol 980 NF) 1.20% w/w, Triethanolamine 0.36% w/w, was prepared according to the manufacturing technique herein described.

Example 48 (Alps001)

A solution composed by Alprazolam 1.09% w/w, Propylene Glycol 98.91% w/w, was prepared according to the manufacturing technique herein described.

Example 49 (Alps002)

A solution composed by Alprazolam 1.06% w/w, Lauric Acid 0.99% w/w, Propylene Glycol 97.95% w/w, was prepared according to the manufacturing technique herein described.

Example 50 (Alps003)

A solution composed by Alprazolam 0.98% w/w, Oleic Acid 1.59% w/w, Propylene Glycol 97.44% w/w, was prepared according to the manufacturing technique herein described.

Example 51 (Alps004)

A solution composed by Alprazolam 1.02% w/w, Oleyl alcohol 1.11% w/w, Propylene Glycol 97.89% w/w, was prepared according to the manufacturing technique herein described.

Example 52 (Alps009)

A solution composed by Alprazolam 1.00% w/w, lauryl alcohol 1.01% w/w, Propylene Glycol 97.99% w/w, was prepared according to the manufacturing technique herein described.

In Vitro Drug Permeation Studies and In Vivo Bioavailability Studies

Figure 1:
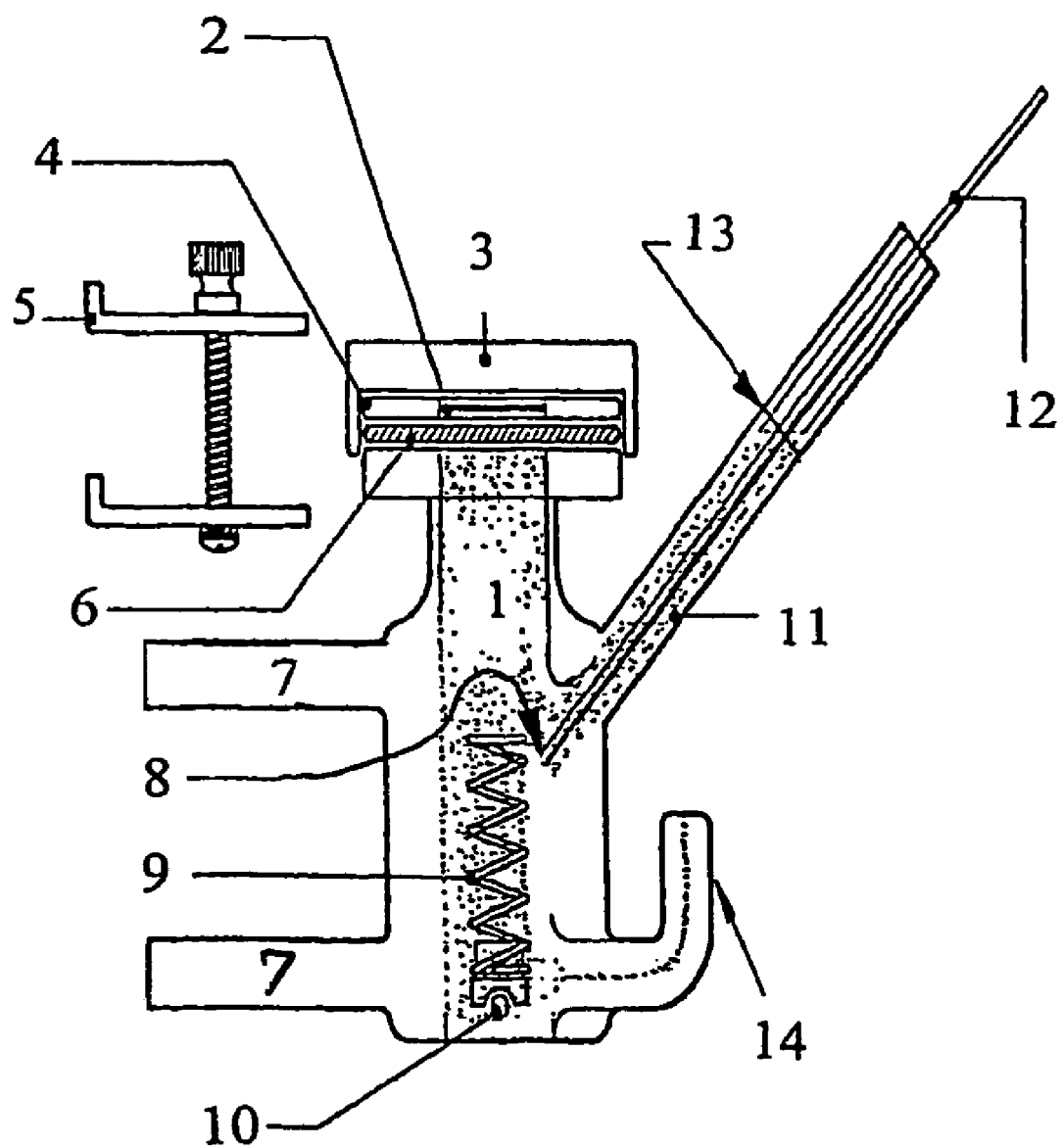
FIG. 1 represents an apparatus "Hanson P/N 57-VC (vertical diffusion cell) 3, is schematically represented wherein:
1=cell receptor
2=donor chamber (dosage area)
3=top plate
4=dosage water
5=clamp
6=membrane
7=water jacket
8=sample point
9=stirring helix
10=magnetic stirrer
11=sample tube
12=sample probe from microette
13=cell level line
14=media replace tube
Typical cell dimensions are: orifice 15 mm, volume 7 ml.
Figure 2:
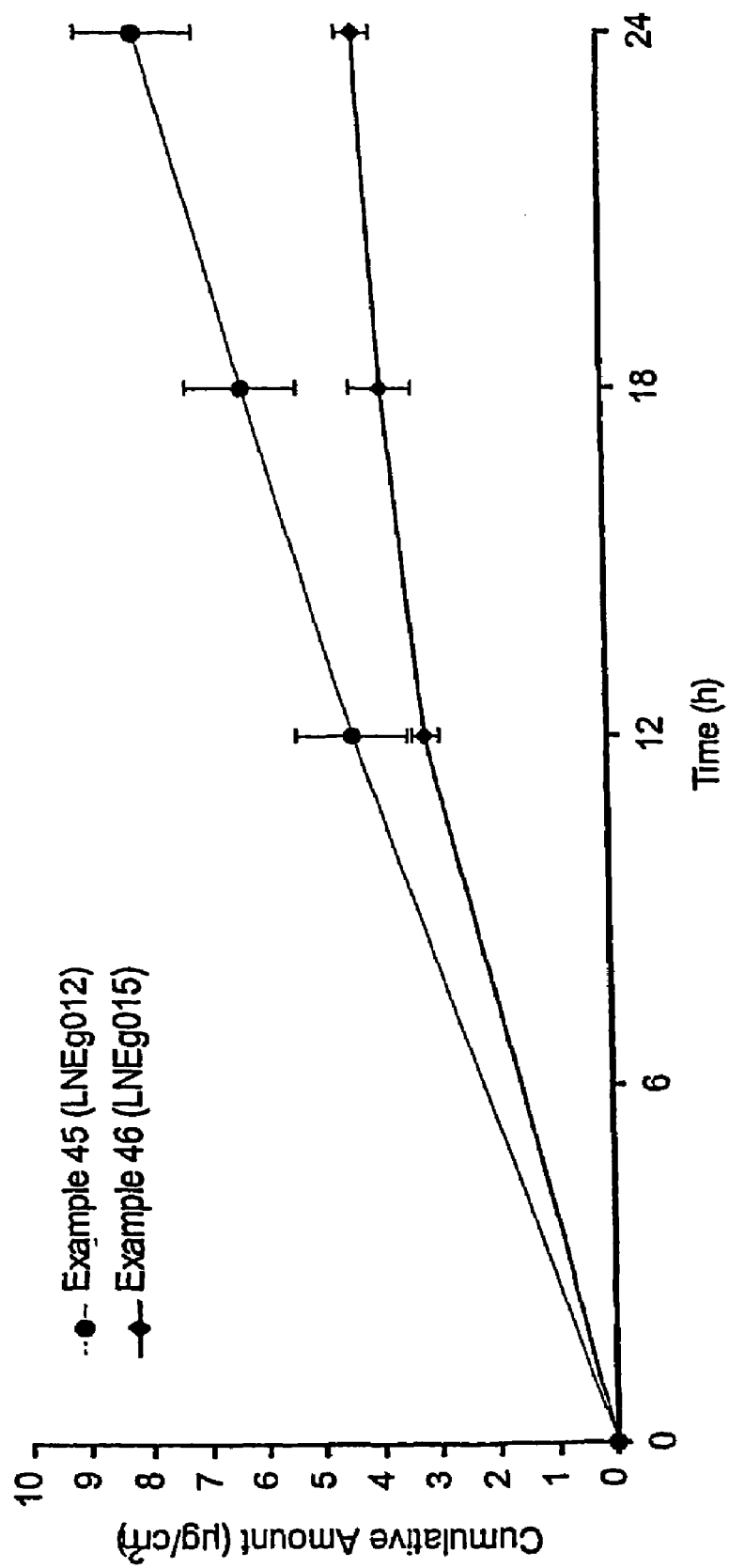
FIG. 2 represents Graphic I relevant to the data from Table II.
Figure 3:
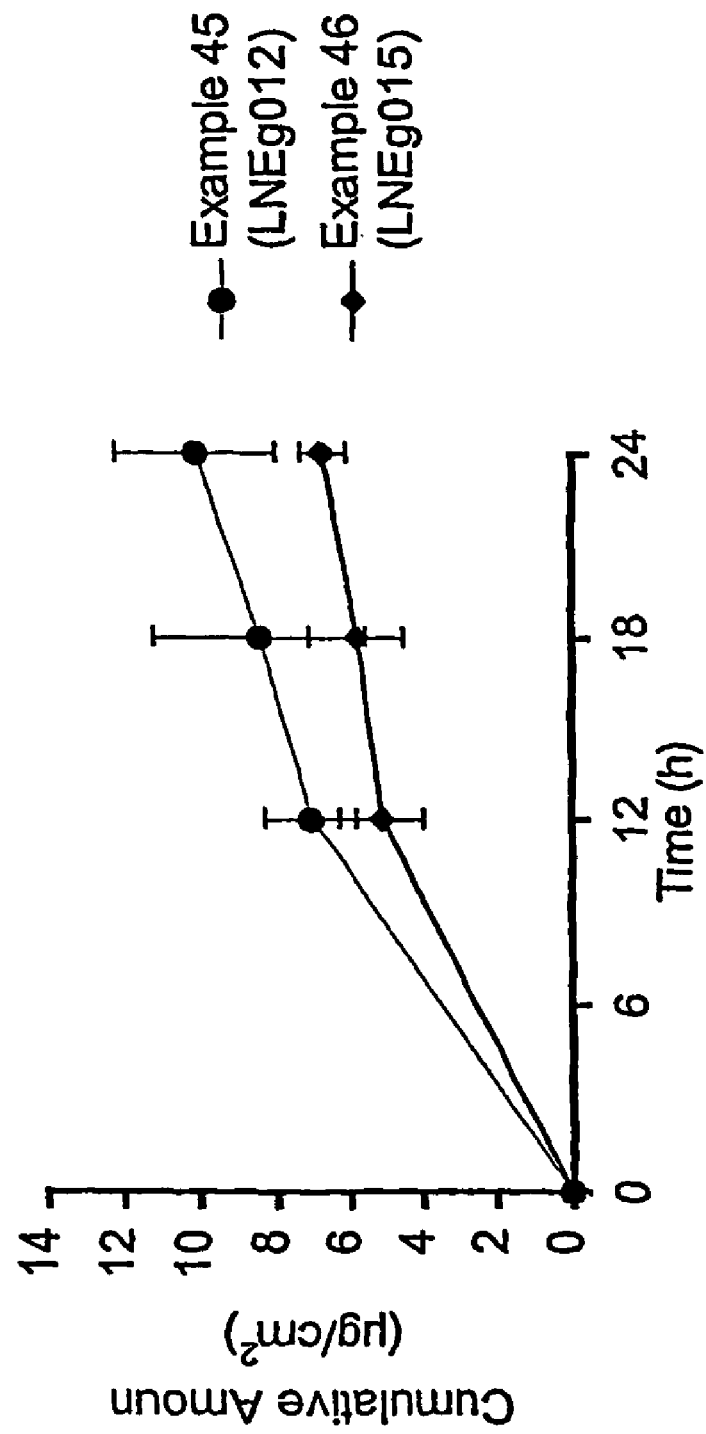
FIG. 3 represents Graphic II relevant to the data from Table IV
Figure 4:
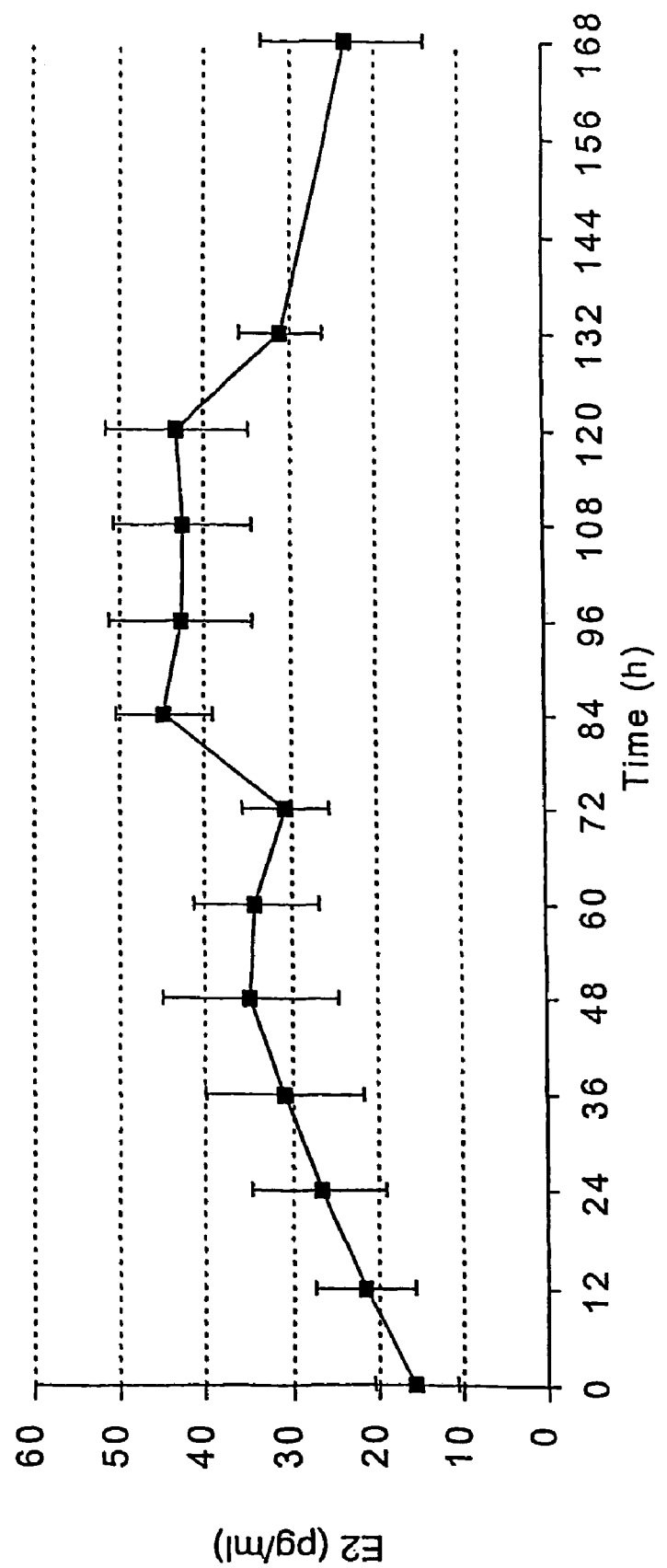
FIG. 4 represents Graphic III relevant to the data from Table V
Figure 5:
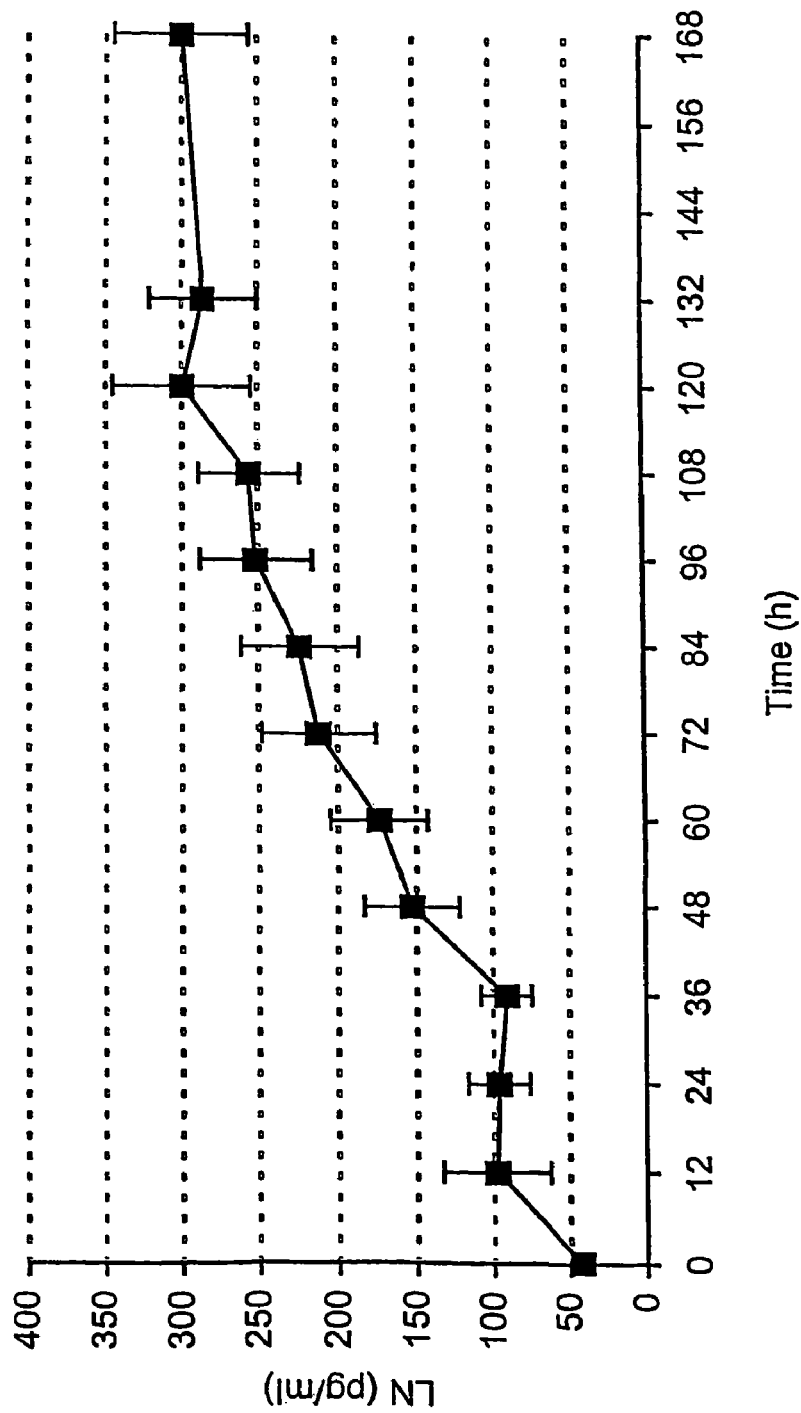
FIG. 5 represents Graphic IV relevant to the data from Table VI
Figure 6:
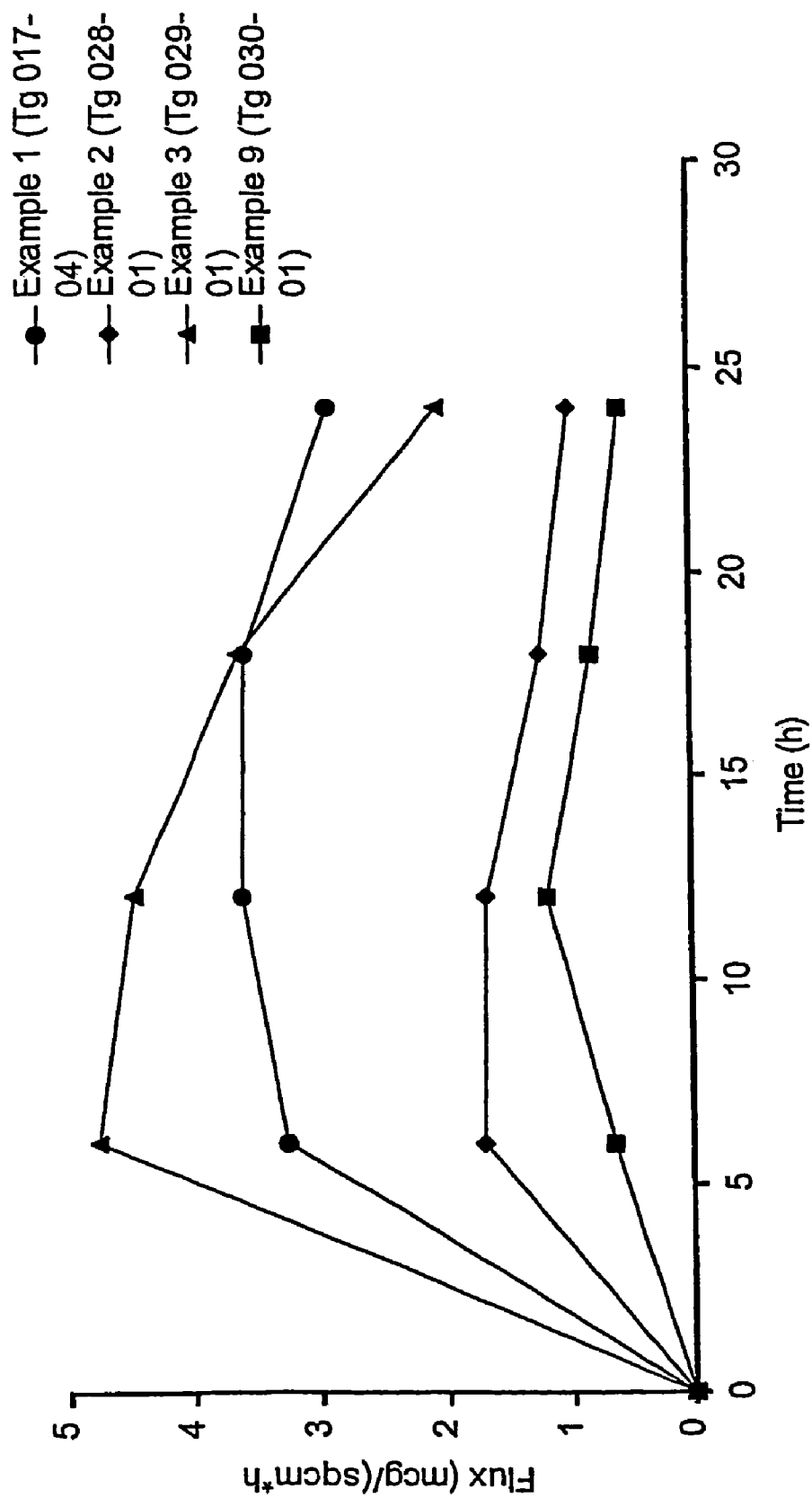
FIG. 6 represents Graphic V relevant to the data from Table VII
Figure 7:
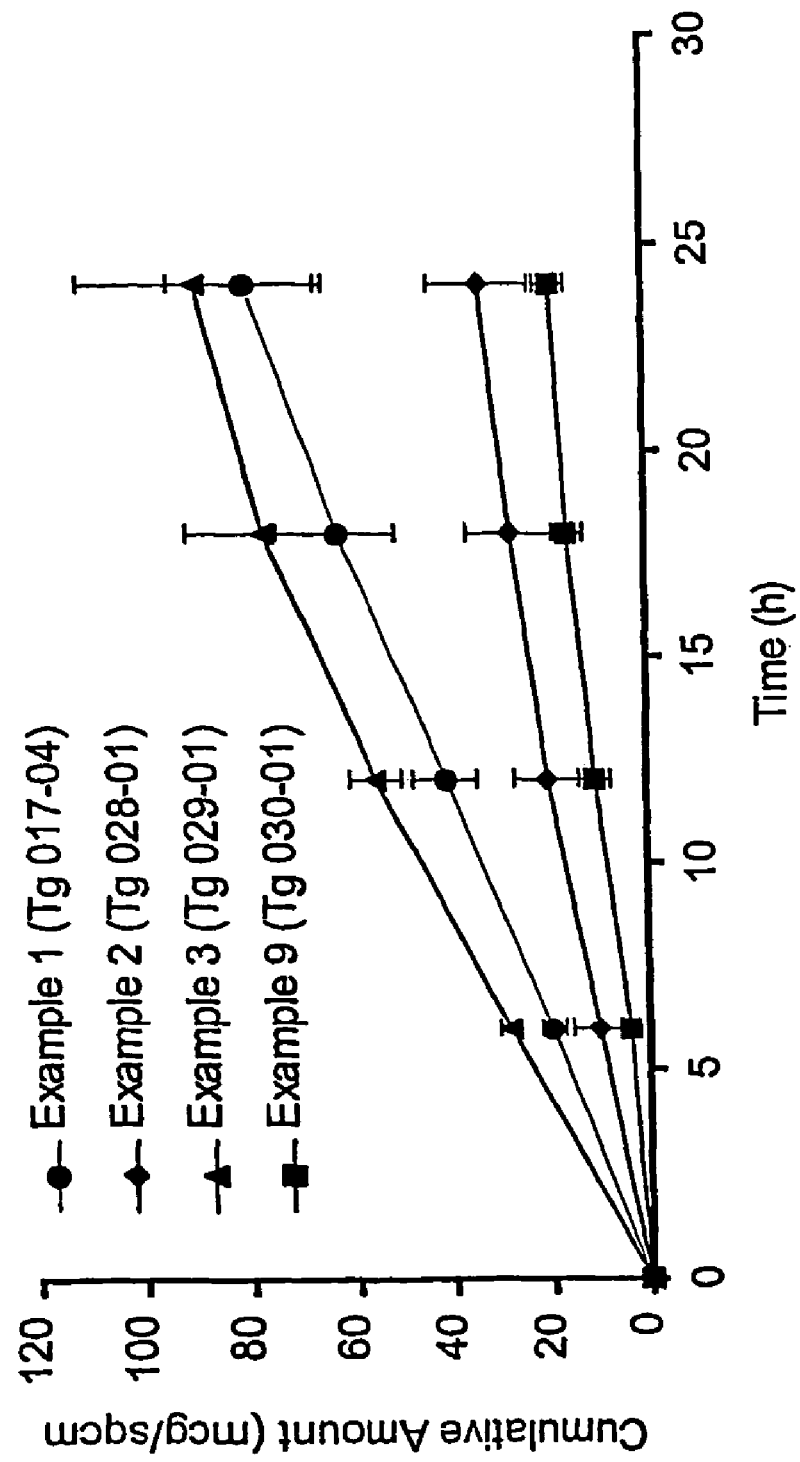
FIG. 7 represents Graphic VI relevant to the data from Table VIII
Figure 8:
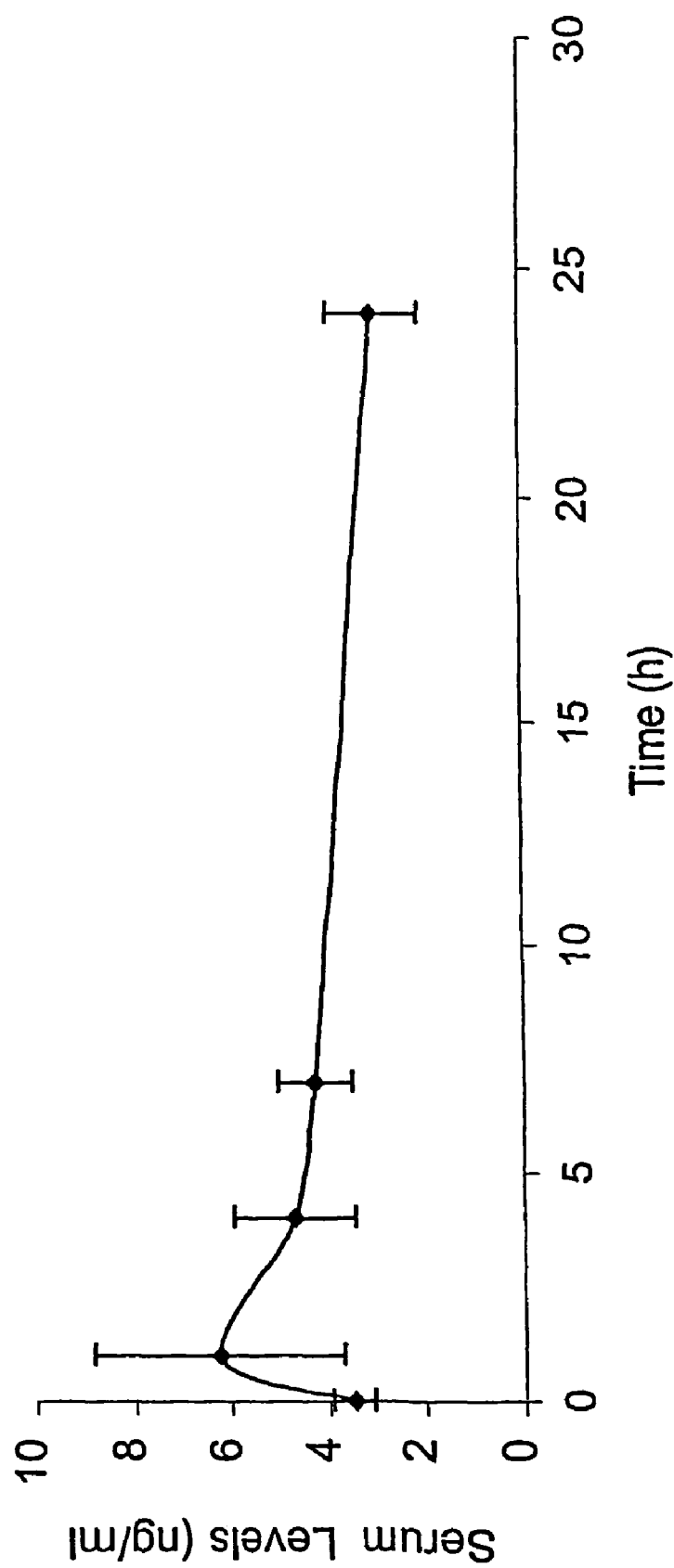
FIG. 8 represents Graphic VII relevant to the data from Table X
Figure 9:
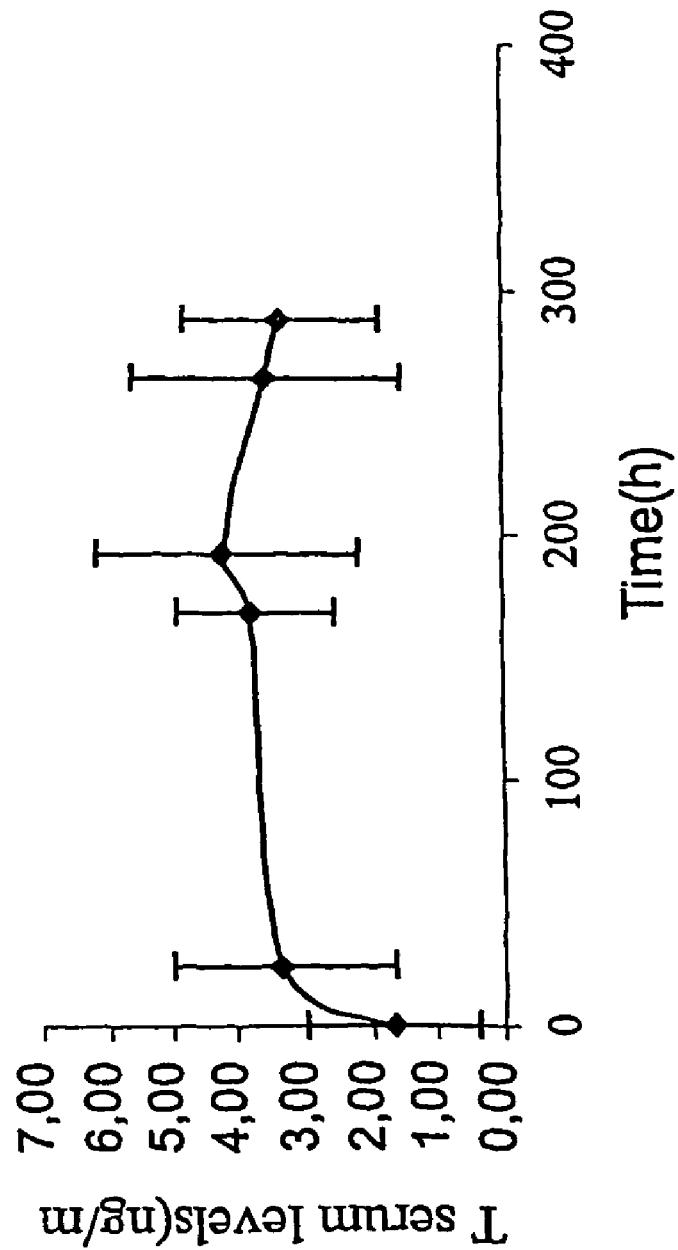
FIG. 9 represents Graphic VII relevant to the data from Table IX
Figure 10:
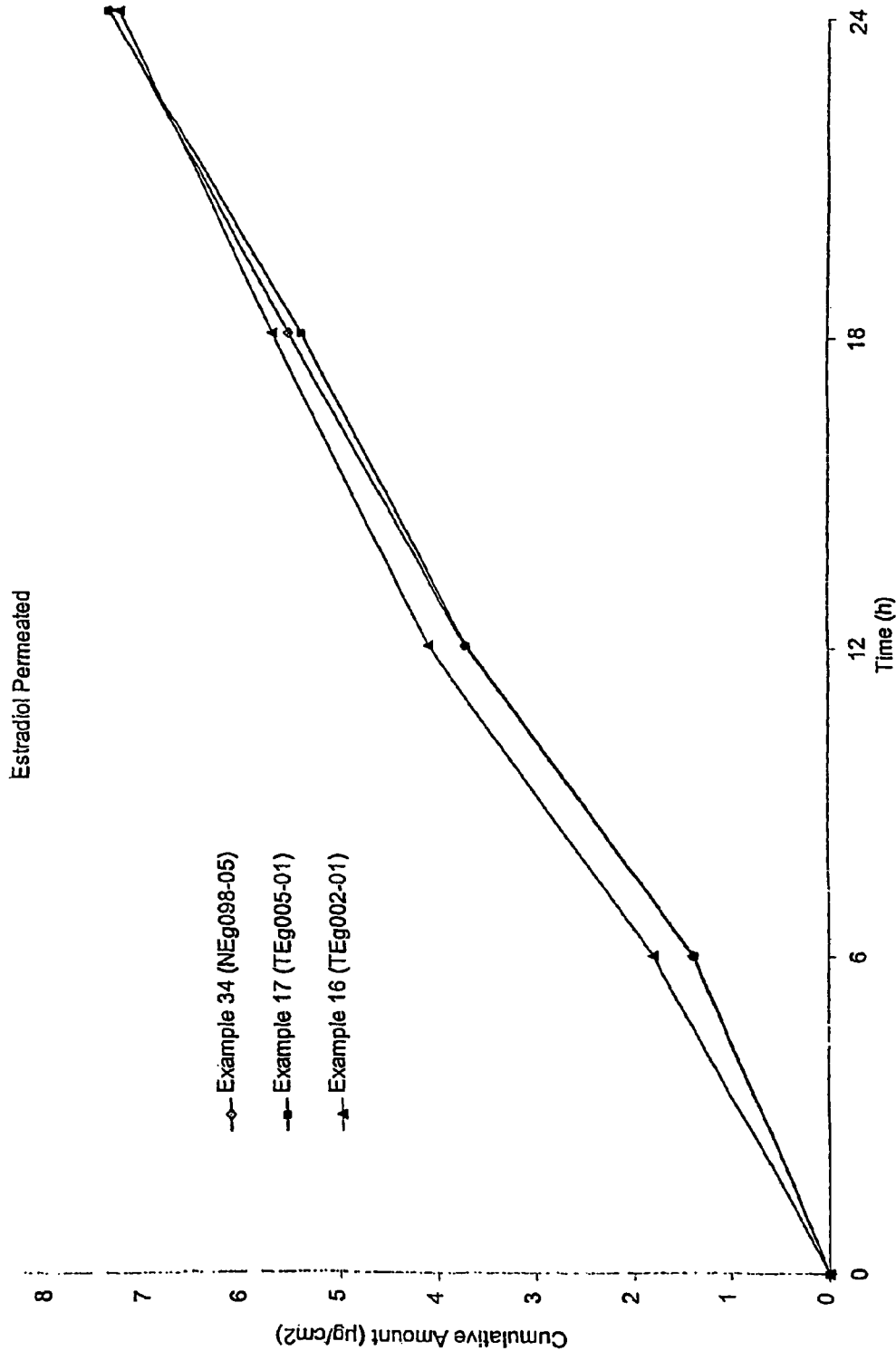
FIG. 10 represents Graphic IX relevant to the data from Table XII
Figure 11:
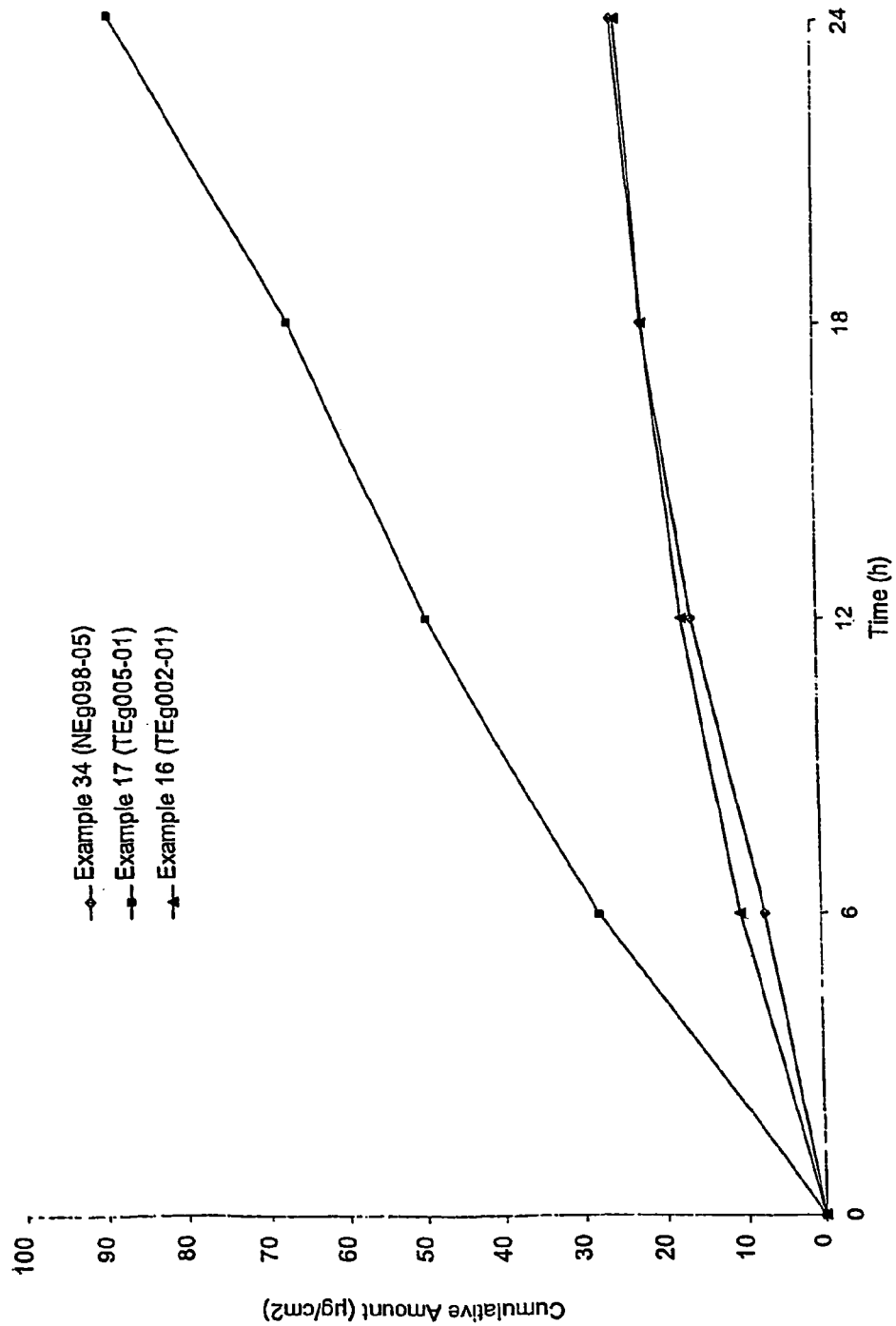
FIG. 11 represents Graphic X relevant to the data from Table XIV
Figure 12:
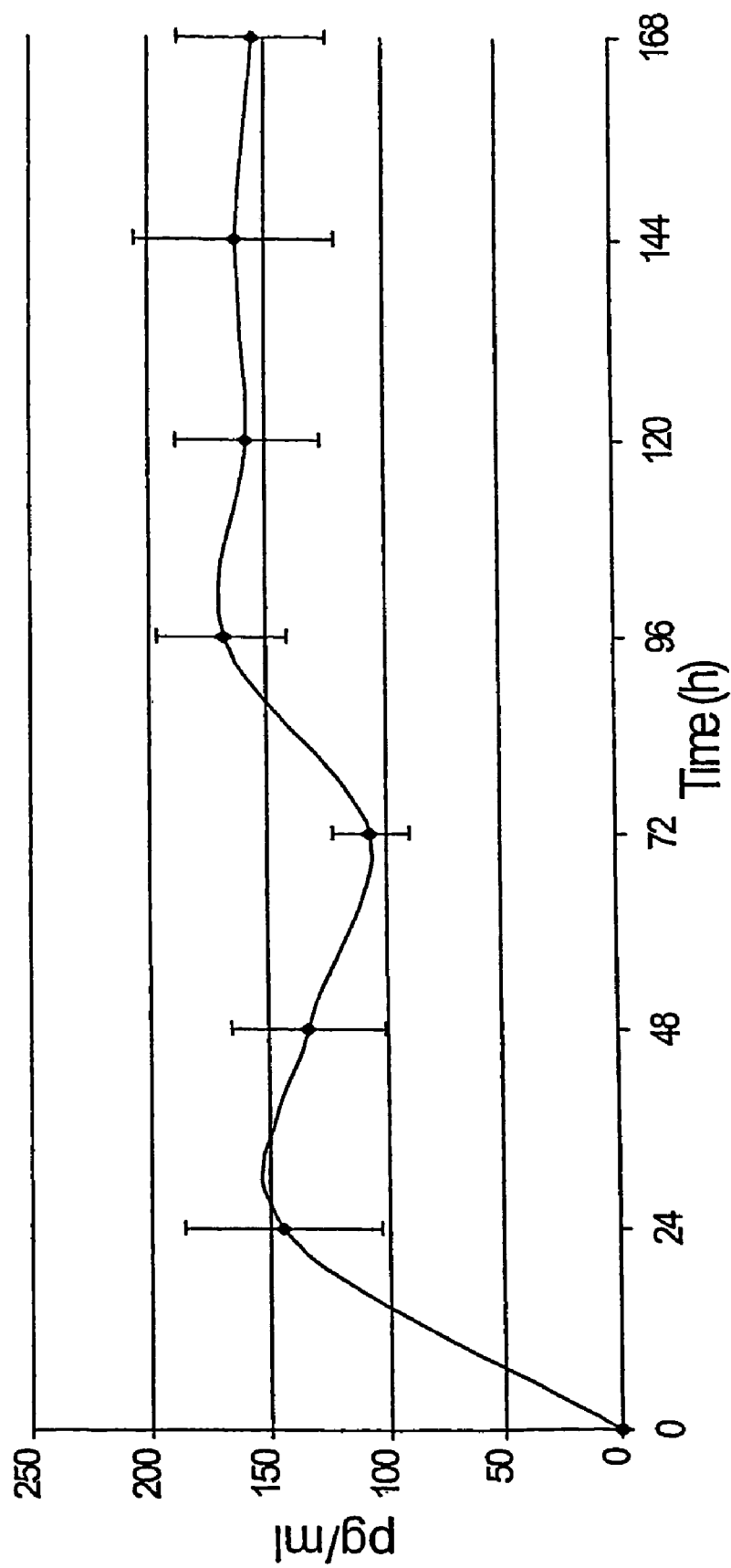
FIG. 12 represents Graphic XI relevant to the data from Table XV
Figure 13:
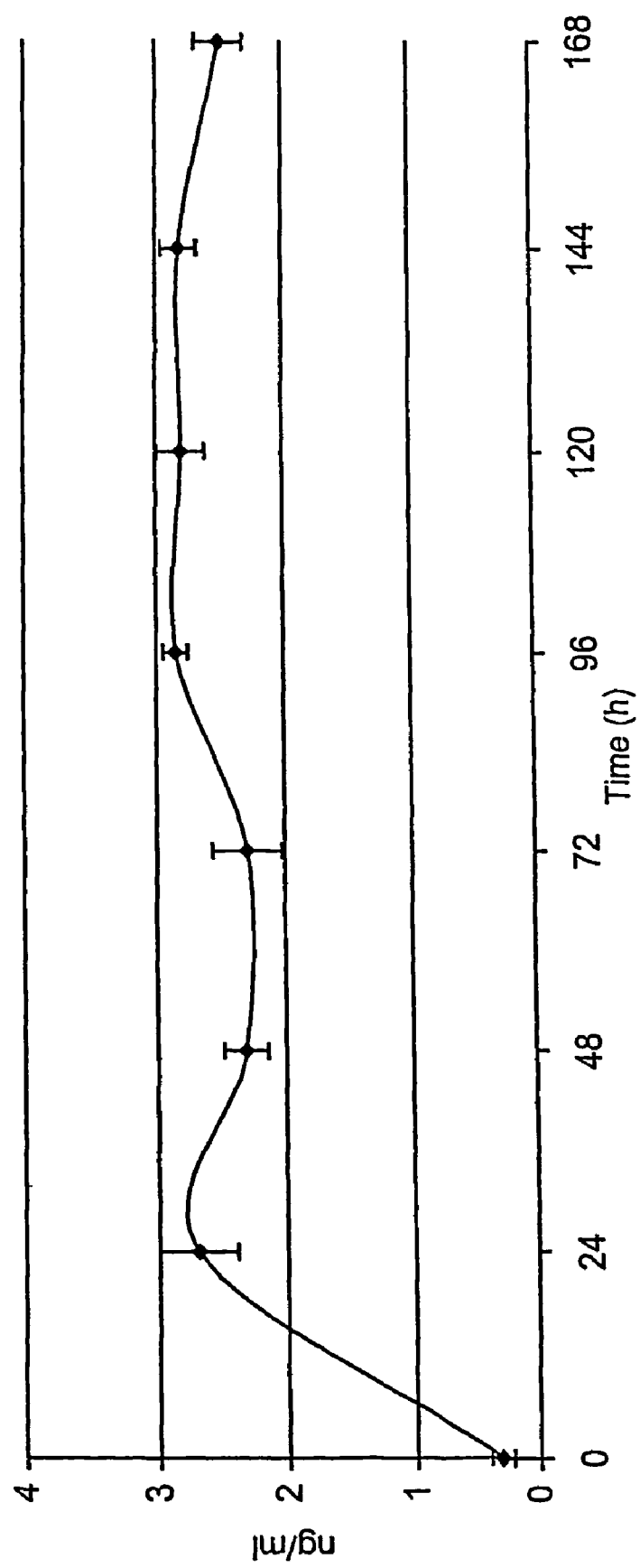
FIG. 13 represents Graphic XII relevant to the data from Table XVI
Figure 14:
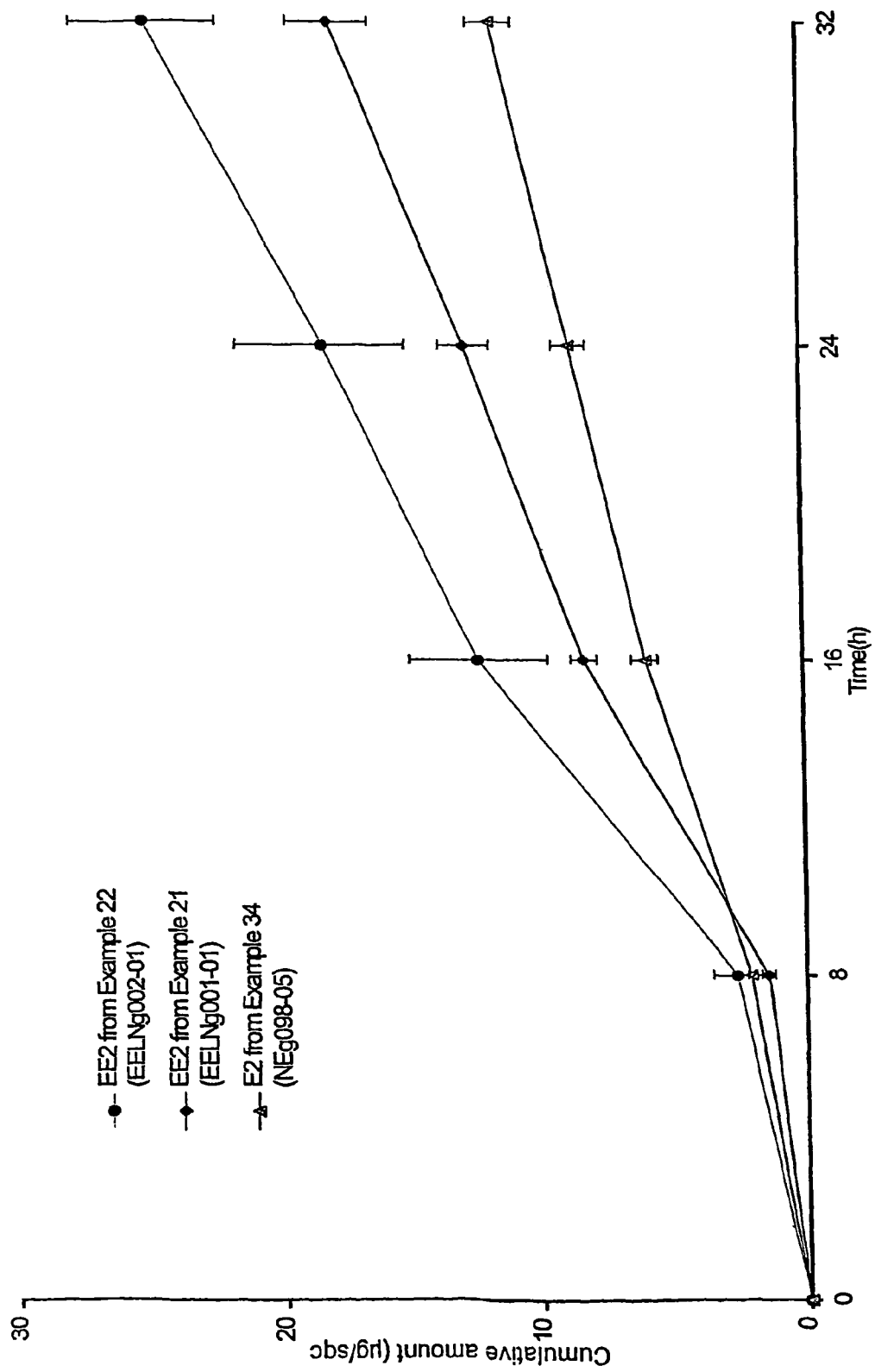
FIG. 14 represents Graphic XIII relevant to the data from Table XVIII
Figure 15:
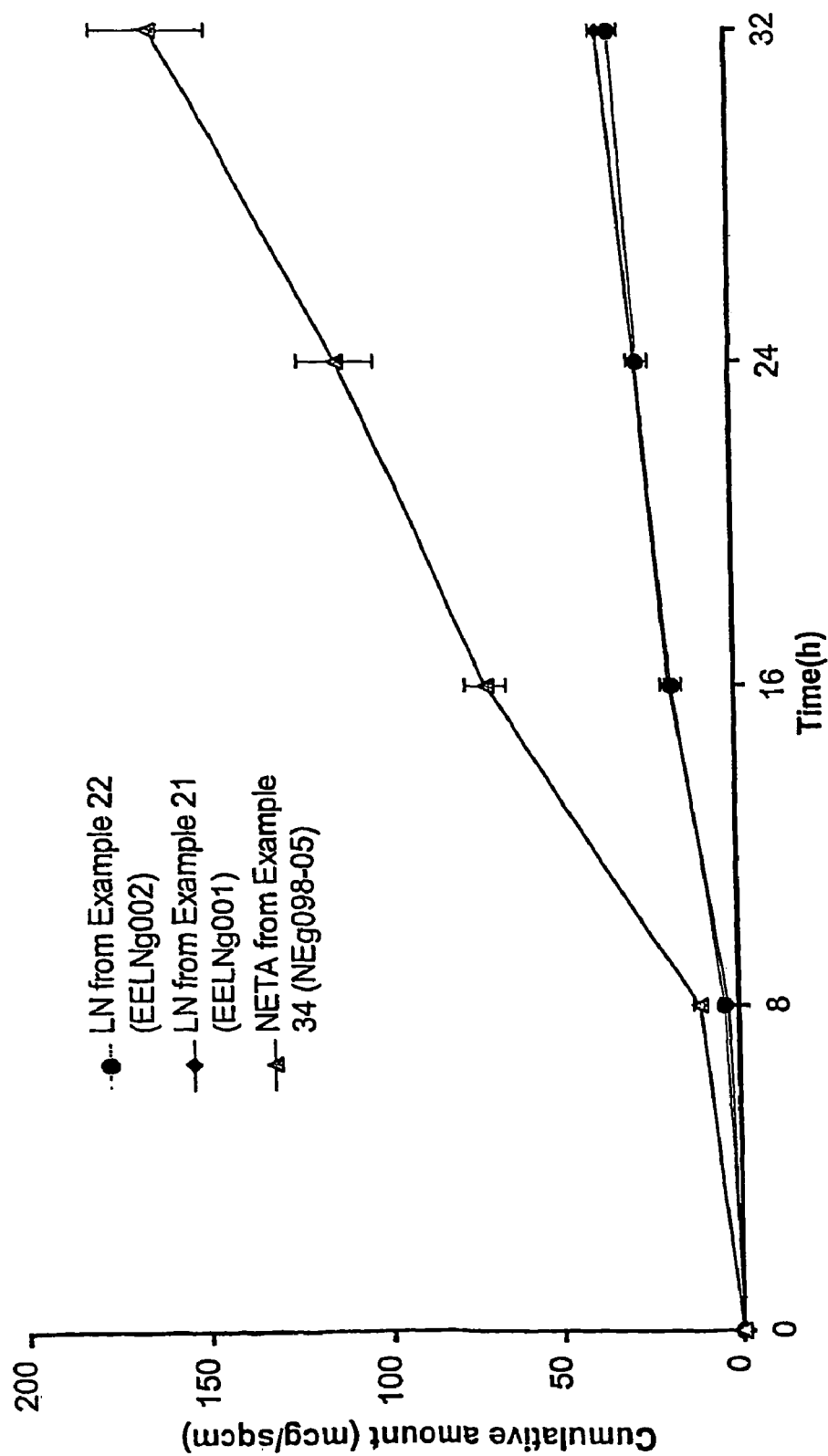
FIG. 15 represents Graphic XIV relevant to the data from Table XX
Figure 16:
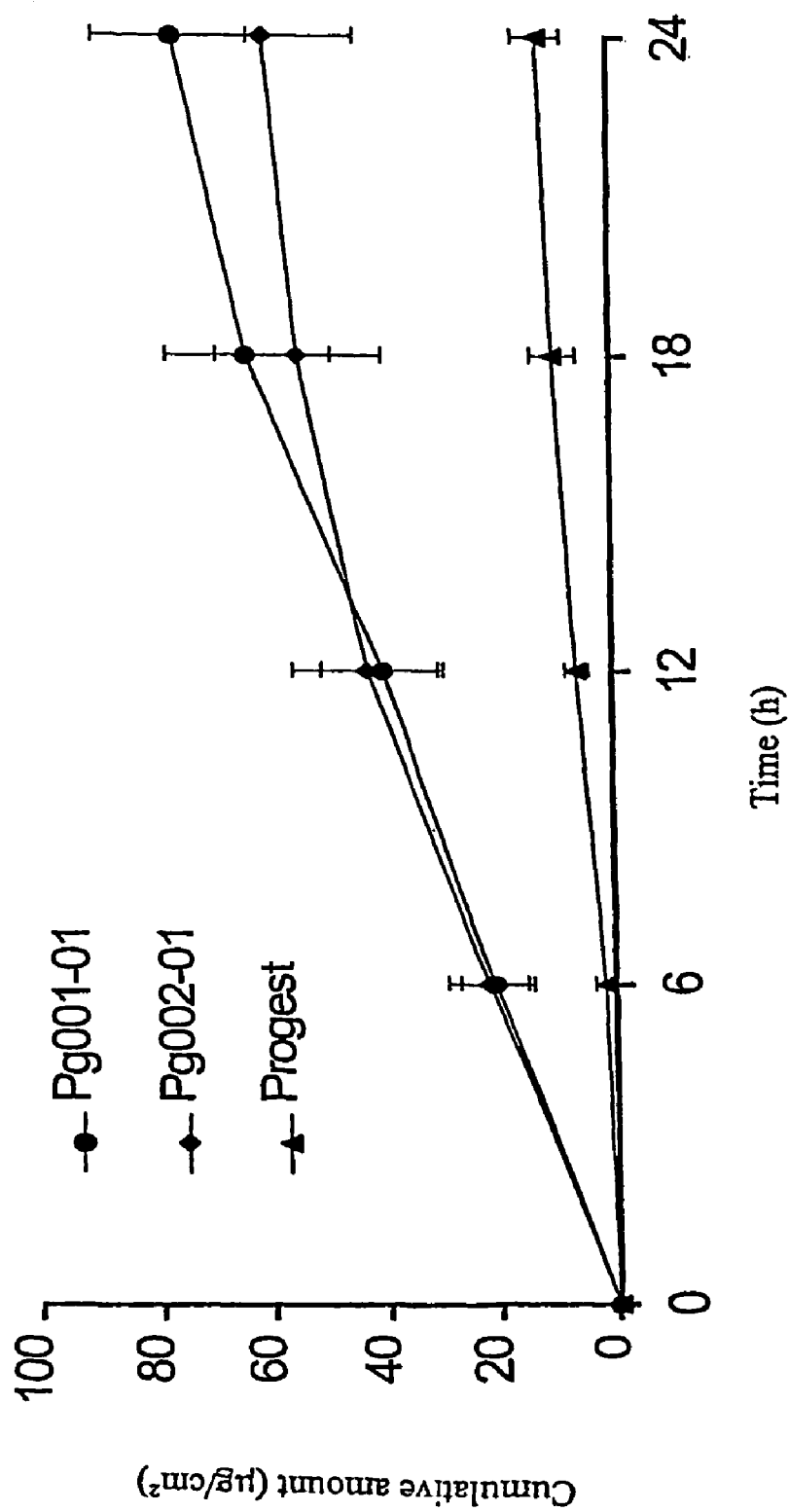
FIG. 16 represents Graphic XV relevant to the data from Table XXII
Figure 17:
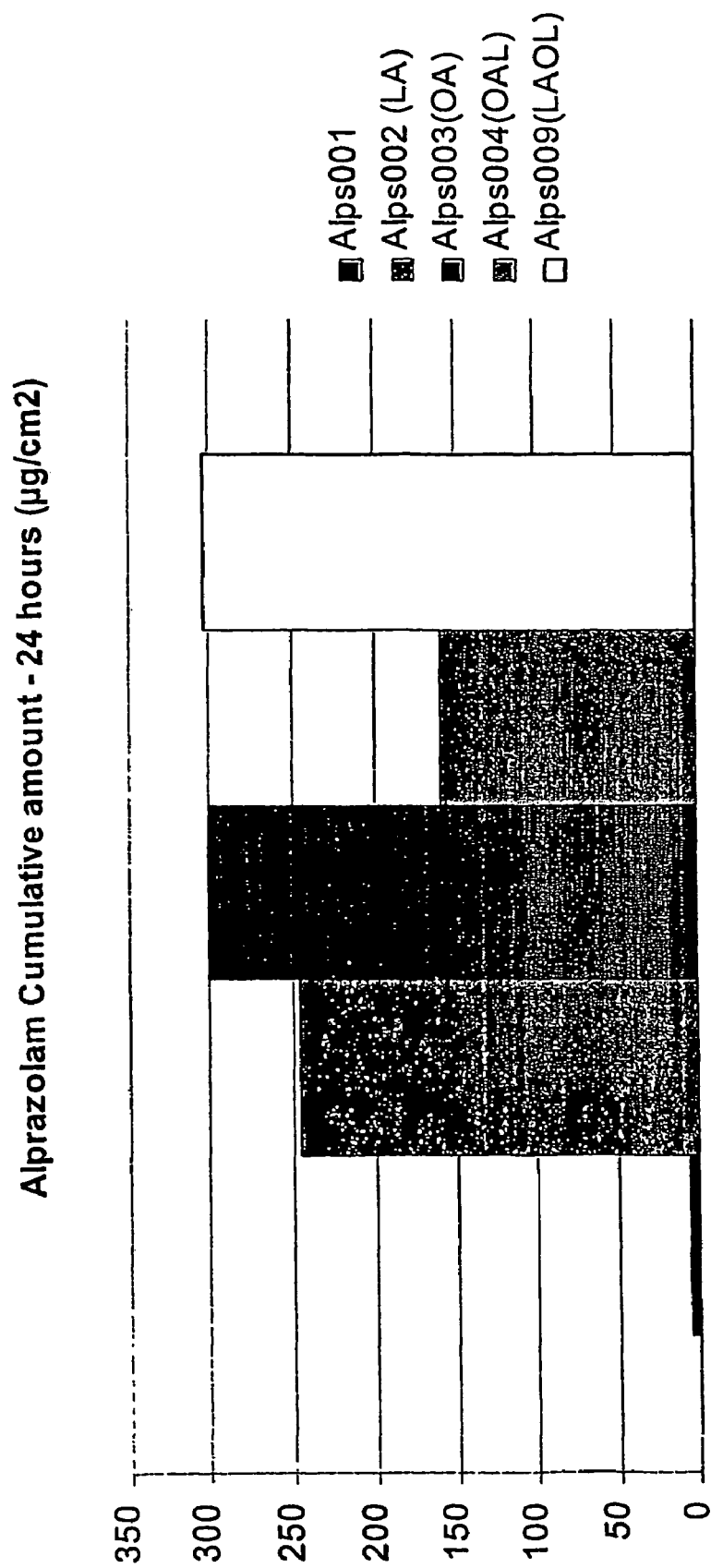
FIG. 17 represents Graphic XVI relevant to the data from Table XXIII
Figure 18:
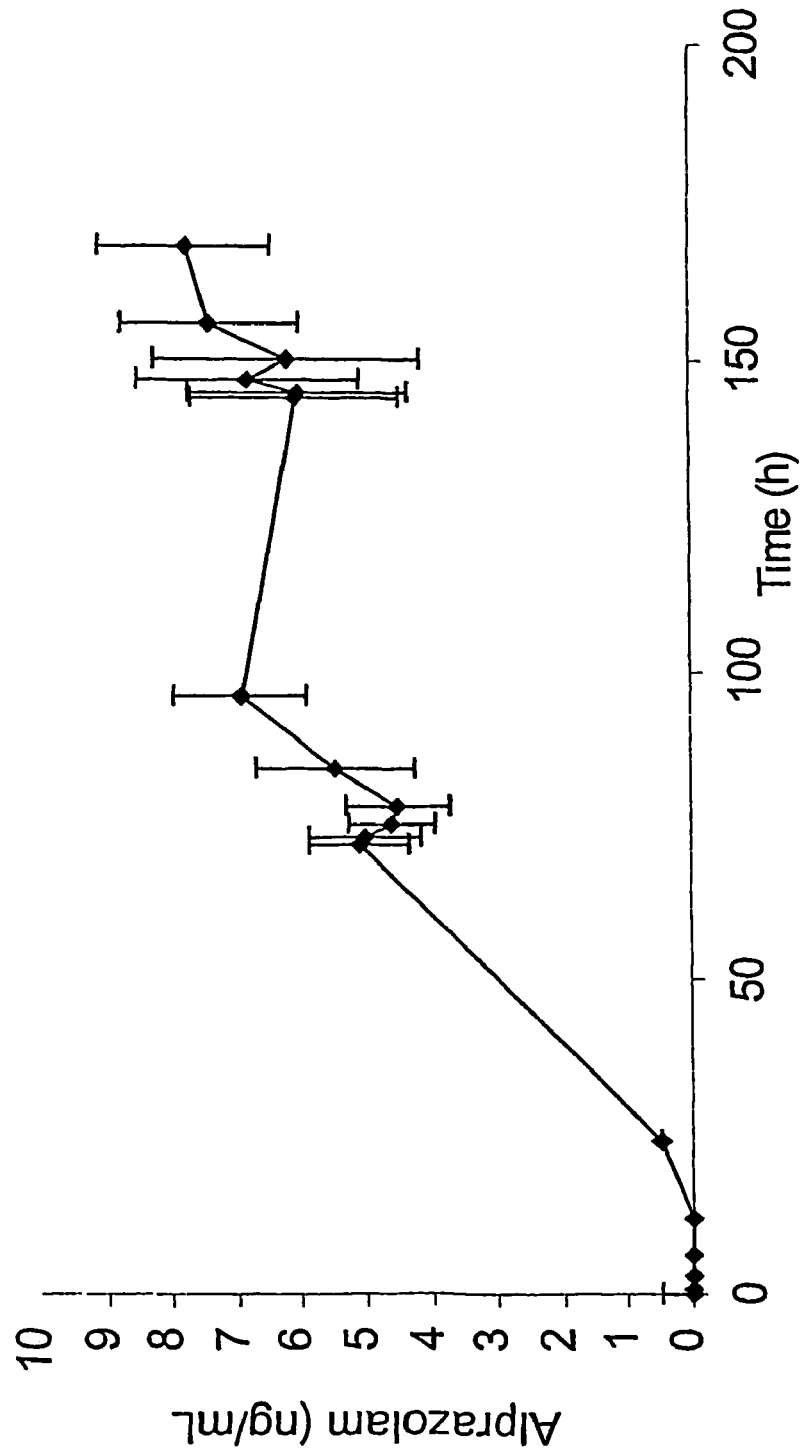
FIG. 18 represents Graphic XVII relevant to the data from Table XXIV
Figure 19:
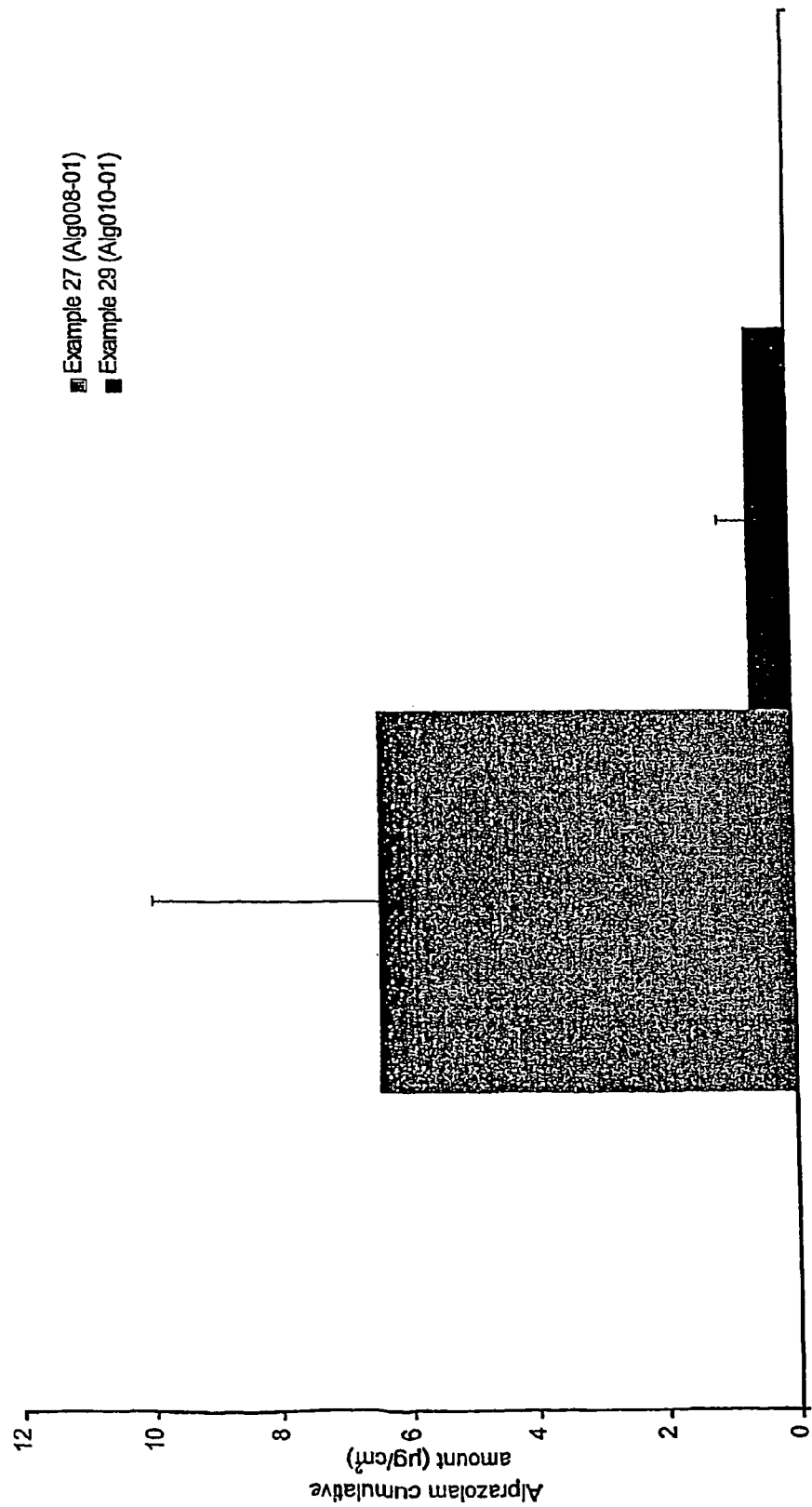
FIG. 19 represents Graphic XVIII relevant to the data from Table XXV
Figure 20:
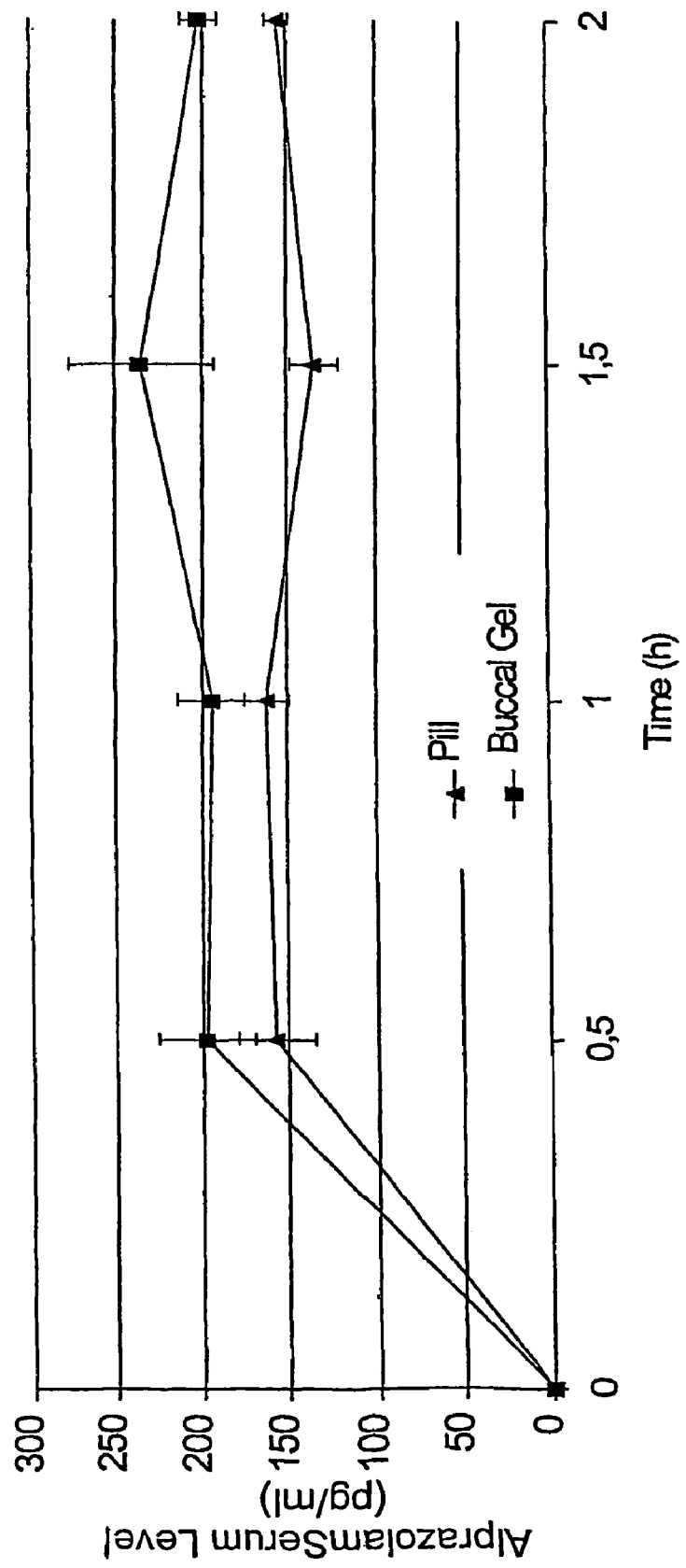

In vitro drug permeation experiments through abdominal guinea pig skin were made using the diffusion chamber that is schematically shown in FIG. 1 (Franz Vertical Diffusion Cell).

Female Guinea pigs, 8 to 16 months of age, were shaved on their abdominal skin 72 hours before sacrificing by cervical dislocation. Only animals that shown absence of lesions were used. A section of full thickness abdominal skin was surgically excised and mounted between the sections of a vertical diffusion cell having 1.77 sqcm of surface area, the epidermal facing up. A given amount of the transdermal devices exemplified previously (10, 25, 50 or 400 mg or 2, 3 ml) was applied over the epidermal layer whilst the dermal layer contact with the receptor solution: 2.0% w/V polyoxyethylene 20 oleyl ether (Oleth 20), with or without PBS, pH 7.4. The receptor chamber was maintained at 35° C. and the studies were conducted under occlusive or non-occlusive conditions and at 600 rpm of stirring speed. At given time points, samples were withdrawn from the receptor solution and the receptor chamber was immediately refilled with fresh solution. All samples were analyzed using a high performance liquid chromatography (HPLC) method.

Flux determination: Transdermal flux (mcg/sqcm/h) was determined from the steady-state slope of the plot of the cumulative amount of the drug(s) permeated through the skin versus time. After steady-state had been established, the linear portion of the plot was used to calculate the flux from the slope.

In order to demonstrate the improvements in the permeation performance applying the invention herein discloses, in vitro permeation studies of examples using the inventive means were compared with examples made without using this invention (without the addition of permeation enhancers).

It was an objective to demonstrate the results obtained applying the invention herein disclose. In the in vitro drug permeation studies the examples using the invention herein claimed were compared with examples made without using this invention (without addition of the permeation enhancers). Also, with some active drugs of the exemplified groups, comparative in vitro permeation studies were done against a reference product, Combi Gels™ NETA (Estradiol+Norethindrone Acetate). Such a product has extensively tested in several human pharmacokinetic tudies (Proceed. Int'l Symp. Control. Rel. Bioact. Mater., 25, CRS, Inc, poster # 5513, 5514 and Proceed. Int'l Symp. Control. Rel. Bioact. Mater., 26, CRS, Inc, poster #5160). Therefore, the comparative in vitro results allow us to consistently predict the in vivo plasmatic level profile for other active agents. Furthermore, preliminary bioavailability studies were carried out for several formulations containing the present invention. Combi Gel ™ is a trademark comprising the invention claimed herein, that means the combination of penetration enhancers.

To further exemplify the invention herein describe, a sorting in groups of active drugs was made, describing in each case the most relevant in vitro and in vivo results that support the present invention. Tables and graphics illustrate the results obtained, furthermore, in vivo studies protocols and the corresponding results obtained are disclosed.

Group A: Hormones

1) Combi Gel™ LN+E2:

A) In vitro permeation study comparing a E2+LN hydroalcoholic gel without using the inventive means against an E2+LN gel containing our invention (Combi Gel™ LN+E2).

Study conditions: Franz Vertical Diffusion Cells (Hanson Research Inc.); Pre-shaved abdominal Guinea pig skin was used as experimental model. The receptor solution was 2% w/w polyoxyethylene 20 oleyl ether (Oleth 20), PBS 10 mM, pH 7.4. The experiments were conducted under non-occlusive conditions, at 35° C. and 600 rpm of stirring speed. Prior to the beginning of the study, the skin pieces were mounted in the permeation cells and maintained at 35° C. in contact with the receptor solution. After loading 50 mg of each formulation over the skin, at the indicated times, 1 ml of the receptor solution was withdrawn, and the receptor chamber was immediately refilled with fresh solution.

TABLE I

In vitro flux of Estradiol
(Slope of cumulative amount of permeated
drug vs. time between 12 and 24 h.)
Mean ± S.D.
In vitro flux ($\mu g/h * cm^2$)
Estradiol

| Example 45<br>(LNEg012-01) (*) | Example 46<br>(LNEg015-01) (**) |
|---|---|
| 0.31 ± 0.04 | 0.10 ± 0.03 |

(*) 0.06% w/w of 17β Estradiol.; 0.09% w/w of Levonorgestrel; with permeation enhancers system

TABLE II

Estradiol in vitro permeation

Estradiol Cumulative Amount
($\mu g/cm^2$)
Mean ± SD

| Time (h) | Example 45<br>(LNEg012) | Example 46<br>(LNEg015) |
|---|---|---|
| 0 | 0 | 0 |
| 12 | 4.42 ± 0.98 | 3.14 ± 0.56 |
| 18 | 6.31 ± 0.98 | 3.86 ± 0.28 |
| 24 | 8.13 ± 1.14 | 4.29 ± 0.87 |

(**) 0.06% w/w of 17β Estradiol.; 0.09% w/w of Levonorgestrel; without permeation enhancers system

TABLE III

In vitro flux of Levonorgestrel
(Slope of cumulative amount of permeated
drug vs. time between 12 and 24 h.)
Mean ± S.D.
In vitro flux ($\mu g/h * cm^2$)

| Example 45<br>(LNEg012-01) (*) | Example 46<br>(LNEg015-01) (**) |
|---|---|
| 0.26 ± 0.10 | 0.14 ± 0.07 |

(*) 0.06% w/w of 17β Estradiol.; 0.09% w/w of Levonorgestrel; with permeation enhancers system
(**) 0.06% w/w of 17β Estradiol.; 0.09% w/w of Levonorgestrel; without permeation enhancers system

TABLE IV

Levonorgestrel in vitro permeation

| | Levonorgestrel Cumulative Amount (μg/cm²), Mean ± SD | |
|---|---|---|
| Time (h) | Example 45 (LNEg012) | Example 46 (LNEg015) |
| 0 | 0 | 0 |
| 12 | 7.10 ± 2.81 | 5.19 ± 1.29 |
| 18 | 8.49 ± 2.11 | 5.85 ± 0.60 |
| 24 | 10.17 ± 2.42 | 6.82 ± 1.22 |

These results show an increment in the cumulative amount permeated of both actives when the invention is present in the formulation (about 2 or 3 times higher). In addition, a more sustained flux of drug can be observed for E2 in that case. This behavior can be attributed, as previously disclosed, to the synergistic combination of the permeation enhancers of the present invention.

Then, a preliminary bioavailability study was carried out in order to further confirm if therapeutic and sustained plasmatic levels of both actives are achieved.

B) Bioavailability Study of Combi Gels™—LN (Experimental Protocol EC006)

Aim

The objective of the study was to evaluate the bioavailability of E2 and LN from an optimized Combi Gel™—LN, in 6 healthy postmenopausal female volunteers.

Study Design
Open labeled, bioavailability study.
Study Drugs: E2 and LN
Product in development: Combi Gel™—LN
Manufactured by: Permatec Laboratorios SA.
Lot.No: LNEg002-01 (Example 43)
Pharmaceutical Dosage Form: Gel.
Route: Transdermal Volunteers: A total of 6 healthy postmenopausal women were selected. All of them completed the study and were submitted to analysis.

Treatment: A single, daily 2.5 g of Combi Gel™—LN application on the external face of the thighs (1.25 g on 400 sqcm of each thigh), during 6 days.

Biological sampling schedule: Venous blood samples were collected immediately prior to (basal value) and at 12, 24, 36, 48, 60, 72, 84, 96, 108, 120, 132, 168 h after the first application of Combi Gel™—LN Analytical assay method: E2 and LN serum levels were assayed using radioimmunoassay.

Results

TABLE V

Serum Levels of Estradiol (pg/ml)

| | Time (h) | | | | | | | | | | | | |
|---|---|---|---|---|---|---|---|---|---|---|---|---|---|
| | 0 | 12 | 24 | 36 | 48 | 60 | 72 | 84 | 96 | 108 | 120 | 132 | 168 |
| Mean | 14 | 19 | 25 | 27 | 30 | 30 | 26 | 38 | 37 | 36 | 37 | 27 | 21 |
| SEM | 5 | 6 | 7 | 9 | 10 | 8 | 6 | 8 | 10 | 10 | 10 | 6 | 9 |

TABLE VI

Serum Levels of Levonorgestrel (pg/ml)

| | Time (h) | | | | | | | | | | | | |
|---|---|---|---|---|---|---|---|---|---|---|---|---|---|
| | 0 | 12 | 24 | 36 | 48 | 60 | 72 | 84 | 96 | 108 | 120 | 132 | 168 |
| Mean | 42 | 98 | 96 | 91 | 152 | 174 | 212 | 224 | 252 | 256 | 300 | 286 | 300 |
| SEM | 4 | 35 | 20 | 16 | 31 | 31 | 36 | 37 | 37 | 33 | 46 | 36 | 45 |

The results herein disclosed clearly demonstrate that both active agents reached therapeutic and sustained plasmatic levels with only one daily application of the transdermal gel tested.

2) Combi Gel™ Testosterone:

A) In vitro permeation study comparing a Testosterone hydroalcoholic gel without including the invention herein disclosed, against a Testosterone gel containing our invention (Combi Gel™ Testosterone): a combination of lauryl alcohol and diethylene glycol monoethyl ether. Two more examples were tested, one containing lauryl alcohol alone as permeation enhancer and the other containing Diethylene glycol monoethyl ether. All examples contains 1.25% w/w of Testosterone.

Study conditions: Franz Vertical Diffusion Cells (Hanson Research Inc.); Pre-shaved abdominal Guinea pig skin was used as experimental model. The receptor solution was 2% w/w polyoxyethylene 20 oleyl ether (Oleth 20), PBS 10 mM, pH 7.4. The experiments were conducted under non-occlusive conditions, at 35° C. and 600 rpm of stirring speed. Prior to the beginning of the study, the skin pieces were mounted in the permeation cells and maintained at 35° C. in contact with the receptor solution. After loading 50 mg of each formulation over the skin, at the indicated times, 1 ml of the receptor solution was withdrawn, and the receptor chamber was immediately refilled with fresh solution.

TABLE VII

Testosterone
In vitro flux (µg/h * cm²)*
Mean ± S.D.

| Example 1 (Tg017-04) | Example 2 (Tg 028-01) | Example 3 (Tg 029-01) | Example 9 (Tg030-01) |
|---|---|---|---|
| 3.27 ± 0.66 | 1.12 ± 0.36 | 2.86 ± 1.51 | 0.70 ± 0.09 |

*(Slope of cumulative amount of permeated drug vs. time between 12 and 24 h.)

Example 1 contains Lauryl alcohol and Diethylene glycol monoethyl ether as permeation enhancers system.

Example 2 contains Diethylene glycol monoethyl ether alone.

Example 3 contains Lauryl alcohol alone

Example 9 contains no permeation enhancers

TABLE VIII

Testosterone
Cumulative Amount (µg/cm²)
Mean ± S.D.

| Time (h) | Example 1 (Tg017-04) | Example 2 (Tg028-01) | Example 3 (Tg029-01) | Example 9 (Tg030-01) |
|---|---|---|---|---|
| 0 | 0 | 0 | 0 | 0 |
| 6 | 19.50 ± 2.30 | 10.25 ± 4.97 | 28.49 ± 1.92 | 3.82 ± 2.04 |
| 12 | 41.20 ± 6.77 | 20.40 ± 6.75 | 55.38 ± 5.34 | 10.90 ± 3.22 |
| 18 | 62.84 ± 11.79 | 27.84 ± 8.70 | 77.31 ± 14.49 | 15.83 ± 2.94 |
| 24 | 80.44 ± 14.61 | 33.80 ± 10.45 | 89.76 ± 22.42 | 19.28 ± 3.16 |

B) Bioavailability Study of Combi Gel™—Testosterone (Experimental Protocol EC009)

Aim

The objective of the study was to evaluate the bioavailability of Testosterone from an optimized Combi Gel™ TESTOSTERONE in 8 hypogonadal volunteers.

Study Design

Open labeled, bioavailability study.

Drug studied: Testosterone

Product in development: Combi Gel™—Testosterone

Lot No: Tg021-02 (same formulation than Example 8)

Manufactured by: Permatec Laboratorios SA.

Pharmaceutical Dosage Form: Gel. Testosterone 1,25% w/w

Route: Transdermal

Volunteers: A total of 8 hypogonadal volunteers were selected. 7 of them completed the study and were submitted to analysis.

Treatment: A single, daily 5.0 g of Combi Gel™—Testosterone application on both shoulders and arms (2.50 g on each shoulder and arm), during 12 days.

Biological sampling schedule: Blood sampling was made each 24 h. During day 1 and 12 a stressed sampling was made.

Analytical assay method: Testosterone serum concentration was determined using RIA.

Results

TABLE IX

Serum Levels of Testosterone (ng/ml)

| | Time (h) | | | | |
|---|---|---|---|---|---|
| | 0 | 24 | 168 | 192 | 264 | 288 |
| Mean | 1.68 | 3.36 | 3.77 | 4.20 | 3.60 | 3.37 |
| SD | 1.30 | 1.69 | 1.22 | 2.02 | 2.06 | 1.47 |

The steady state was reached during the $2^{nd}$ day. Testosterone steady state were maintained between 48 and 288 h. Mean testosterone serum level within this period was 3.73+/− 1.70 ng/mL.

TABLE X

Pharmacokinetic parameters of testosterone, after repeated administration of a transdermal gel containing testosterone in 7 healthy volunteers (Mean values)

| AUC (ng * h/ml) | 79.6 +/− 33.7 |
|---|---|
| Cmax (ng/ml) | 6.1 +/− 2.7 |
| Tmax (h) | 1.9 +/− 1.5 |
| Daily dose (mg) | 4.3 +/− 1.8 |

Calculation made on the last 24 h values of the study

3) Combi Gel™ Testosterone/Estradiol:

A) In order to further evaluate the feasibility of a combination gel containing Testosterone+Estradiol containing the invention herein disclosed, an in vitro permeation study comparing a Combi Gel Testosterone+Estradiol against a Norethindrone Acetate+Estradiol composition disclosed in the U.S. Pat. No. 5,891,462 was carried out.

Study conditions: Franz Vertical Diffusion Cells (Hanson Research Inc.); Pre-shaved abdominal Guinea pig skin was used as experimental model. The receptor solution was 2% w/w polyoxyethylene 20 oleyl ether (Oleth 20), PBS 10 mM, pH 7.4. The experiments were conducted under non-occlusive conditions, at 35° C. and 600 rpm of stirring speed. Prior to the beginning of the study, the skin pieces were mounted in the permeation cells and maintained at 35° C. in contact with the receptor solution. After loading 50 mg of each formulation over the skin, at the indicated times, 1 ml of the receptor solution was withdrawn, and the receptor chamber was immediately refilled with fresh solution.

TABLE XI

In vitro flux of Estradiol
(Slope of cumulative amount of permeated
drug vs. time between 6 and 24 h.)
Mean ± S.D.
In vitro flux (µg/h * cm²)
Estradiol

| Example 34 (NEg098-05) (*) | Example 17 (TEg005-01) (*) | Example 16 (TEg002-01) (*) |
|---|---|---|
| 0.27 ± 0.03 | 0.31 ± 0.01 | 0.27 ± 0.03 |

(*) Contains 0.06% w/w of 17β Estradiol.

TABLE XII

Estradiol in vitro permeation

| | Cumulative Amount (µg/cm$^2$) Mean ± SD | | |
|---|---|---|---|
| Time (h) | Example 34 (NEg098-05) | Example 17 (TEg005-01) | Example 16 (TEg002-01) |
| 0 | 0 | 0 | 0 |
| 6 | 1.39 ± 0.36 | 1.38 ± 0.53 | 1.80 ± 0.19 |
| 12 | 3.73 ± 0.35 | 3.71 ± 1.12 | 4.12 ± 0.23 |
| 18 | 5.57 ± 0.81 | 5.43 ± 1.30 | 5.74 ± 0.41 |
| 24 | 7.46 ± n.a. | 7.48 ± 1.26 | 7.37 ± 0.47 | n.a. means not available

TABLE XIII

In vitro flux of Testosterone and Norethindrone Acetate
(Slope of cumulative amount of permeated
drug vs. time between 6 and 24 h.)
Mean ± S.D.
In vitro flux (µg/h * cm$^2$)

| Norethindrone Acetate | Testosterone | |
|---|---|---|
| Example 34 (NEg098-05) (1) | Example 17 (TEg005-01) (2) | Example 16 (TEg002-01) (3) |
| 1.21 ± 0.12 | 3.35 ± 0.04 | 0.65 ± 0.34 |

(1) Contains 1.20% w/w of Norethindrone Acetate.
(2) Contains 0.60% w/w of Testosterone
(3) Contains 0.18% w/w of Testosterone

TABLE XIV

Testosterone and Norethindrone Acetate in vitro permeation

| | Cumulative Amount (µg/cm$^2$) Mean ± SD | | |
|---|---|---|---|
| Time (h) | Norethindrone Acetate Example 34 (NEg098-05) | Testosterone Example 17 (TEg005-01) | Testosterone Example 16 (TEg002-01) |
| 0 | 0 | 0 | 0 |
| 6 | 7.37 ± 2.76 | 27.96 ± 6.04 | 10.44 ± 0.41 |
| 12 | 16.00 ± 3.41 | 49.58 ± 7.51 | 17.31 ± 1.73 |
| 18 | 21.90 ± 3.68 | 67.21 ± 9.87 | 21.75 ± 3.09 |
| 24 | 25.53 ± 4.69 | 89.77 ± 7.96 | 25.10 ± 5.83 |

The formulation containing Testosterone 0,60% w/w and Estradiol 0,060% w/w (Example 17) was selected for its evaluation in a preliminary bioavailability study.

B) Bioavailability Study of Combi Gel™—Testosterine+Estradiol (Experimental Protocol EC012)

Aim

The objective of the study was to evaluate the bioavailability of Testosterone and Estradiol from an optimized Combi Gel™ TESTOSTERONE+ESTRADIOL in 6 healthy postmenopausal women volunteers.

Study Design

Open labeled, bioavailability study.

Drugs Studied: Testosterone+Estradiol

Product in development: Combi Gel™—Testosterone+Estradiol

Manufactured by: Permatec Laboratorios SA

Lot No: Tegtb 007-02, same composition as Example 17 (TEg005-01)

Pharmaceutical Dosage Form: Gel. Testosterone 0.60% w/w+Estradiol 0.060% w/w.

Route: Transdermal

Volunteers: A total of 6 healthy postmenopausal women were selected. All of them completed the study and were submitted to analysis.

Treatment: A single, daily 5.0 g of Combi Gel™—Testosterone+Estradiol application on shoulders and arms (2.50 g on each shoulder and arm), during 6 days.

Biological sampling schedule: Venous blood samples were collected immediately prior to (basal value) and at 24, 48, 72, 96, 120, 144, 146, 150, 156, 168 h after the first application of Combi Gel™ TestoE2.

Analytical assay method: E2 serum levels were assayed using immunofluorescence and Testosterone serum levels were assayed using radioimmunoassay.

Results

TABLE XV

Serum Levels of Estradiol (pg/ml)

| | Time (h) | | | | | | | | | | |
|---|---|---|---|---|---|---|---|---|---|---|---|
| | 0 | 24 | 48 | 72 | 96 | 120 | 144 | 146 | 150 | 156 | 168 |
| Mean | 25.00 | 144.50 | 133.41 | 105.91 | 168.96 | 157.87 | 162.60 | 133.12 | 116.25 | 72.17 | 155.38 |
| SEM | — | 41.59 | 33.05 | 16.43 | 27.80 | 30.73 | 43.11 | 29.13 | 19.19 | 16.10 | 32.47 |

TABLE XVI

Serum Levels of Testosterone (ng/ml)

| | Time (h) | | | | | | | | | | |
|---|---|---|---|---|---|---|---|---|---|---|---|
| | 0 | 24 | 48 | 72 | 96 | 120 | 144 | 146 | 150 | 156 | 168 |
| Mean | 0.31 | 2.70 | 2.32 | 2.30 | 2.85 | 2.80 | 2.82 | 3.45 | 2.88 | 2.28 | 2.50 |
| SEM | 0.09 | 0.30 | 0.17 | 0.28 | 0.09 | 0.18 | 0.14 | 0.36 | 0.27 | 0.20 | 0.19 |

Both active agents achieved sustained and controlled plasmatic levels utilizing the invention means herein claimed. Although, the plasmatic levels of both active agents are near to the upper limit of the therapeutic window. Therefore, less dosage or less concentration of the active drugs would be tested in future clinical studies.

4) Combi Gel™ Levonorgestrel/Ethynil Estradiol

A) In order to further evaluate the feasibility of a combination gel containing L-Norgestrel+Ethynil Estradiol and the invention herein disclosed, an in vitro permeation study comparing two Combi Gel L-Norgestrel+Ethynil Estradiol (with different content in Ethynil Estradiol) against a Combi Gel Norethindrone Acetate+Estradiol already disclosed in the U.S. Pat. No. 5,891,462 was carried out.

Study conditions: Franz Vertical Diffusion Cells (Hanson Research Inc.); Pre-shaved abdominal Guinea pig skin was used as experimental model. The receptor solution was 2% W/W polyoxyethylene 20 oleyl ether (Oleth 20). The experiments were conducted under occlusive conditions, at 35° C. and 600 rpm of stirring speed. Prior to the beginning of the study, the skin pieces were mounted in the permeation cells and maintained at 35° C. in contact with the receptor solution. After loading 400 mg of each formulation over the skin, at the indicated times, 1 ml of the receptor solution was withdrawn, and the receptor chamber was immediately refilled with fresh solution.

TABLE XVII

In vitro flux of Estrogens
(Slope of cumulative amount of permeated drug vs. time between 16 and 32 h.)
Mean ± S.D.
In vitro flux ($\mu g/h * cm^2$)

| Estradiol Example 34 (NEg098-05) (1) | Ethynil Estradiol Example 21 (EELNg001-01) (2) | Ethynil Estradiol Example 22 (EELNg002-01) (3) |
|---|---|---|
| 0.36 ± 0.03 | 0.62 ± 0.07 | 0.80 ± 0.03 |

(1) Contains 0.06% w/w of Estradiol
(2) Contains 0.06% w/w of Ethynil Estradiol
(3) Contains 0.09% w/w of Ethynil Estradiol

TABLE XVIII

Estrogens in vitro permeation
Estrogens Cumulative Amount ($\mu g/cm^2$), Mean ± SD

| Time (h) | Estradiol Example 34 (NEg098-05) (1) | Ethynil Estradiol Example 21 (EELNg001-01) (2) | Ethynil Estradiol Example 22 (EELNg002-01) (3) |
|---|---|---|---|
| 0 | 0 | 0 | 0 |
| 8 | 2.03 ± 0.12 | 1.42 ± 0.22 | 2.58 ± 0.81 |
| 16 | 6.00 ± 0.49 | 8.36 ± 0.50 | 12.40 ± 2.41 |
| 24 | 8.83 ± 0.65 | 12.90 ± 0.99 | 18.54 ± 3.06 |
| 32 | 11.82 ± 0.89 | 18.28 ± 1.56 | 25.21 ± 2.82 |

TABLE XIX

In vitro flux of Progestagens
(Slope of cumulative amount of permeated drug vs. time between 16 and 32 h.)
Mean ± S.D.
In vitro flux ($\mu g/h * cm^2$)

| Norethindrone Acetate Example 34 (NEg098-05) (4) | Levonorgestrel Example 21 (EELNg001-01) (5) | Levonorgestrel Example 22 (EELNg002-01) (6) |
|---|---|---|
| 5.95 ± 0.59 | 1.14 ± 0.09 | 0.98 ± 0.03 |

(4) Contains 1.20% w/w of Norethindrone Acetate
(5) Contains 9.09% w/w of Levonorgestrel
(6) Contains 0.09% w/w of Levonorgestrel

TABLE XX

Progestagens in vitro permeation
Progestogens Cumulative Amount ($\mu g/cm^2$), Mean ± SD

| Time (h) | Norethindrone Acetate Example 34 (NEg098-05) (1) | Levonorgestrel Example 21 (EELNg001-01) (2) | Levonorgestrel Example 22 (EELNg002-01) (3) |
|---|---|---|---|
| 0 | 0 | 0 | 0 |
| 8 | 11.06 ± 1.59 | 3.02 ± 0.39 | 3.91 ± 0.93 |
| 16 | 70.42 ± 5.80 | 18.07 ± 1.19 | 17.72 ± 2.70 |
| 24 | 113.18 ± 10.71 | 26.86 ± 1.84 | 25.79 ± 3.28 |
| 32 | 165.67 ± 15.22 | 36.36 ± 2.16 | 33.42 ± 2.73 |

These results shown a similar behavior and permeation profile when compared with other examples previously described containing Levonorgestrel and Estradiol, then, we can conclude that an enhancement factor was achieved also in the present examples.

Also, these results suggests that a combination Ethynil Estradiol+Levonorgestrel Gel is considered feasible, since a prediction of in vivo fluxes for both actives when it was compared with Combi Gel NETA+E2 (example 34) concluded to be very close to the recommended daily doses. That means, about 50 µg/day for Ethynil Estradiol and 200-300 µg/day for Levonorgestrel.

5) Combi Gel™ Progesterone

A) In order to further evaluate the feasibility of a gel containing natural Progesterone Progesterone) and utilizing the invention herein disclosed, an in vitro permeation study comparing two different examples of Combi Gel Progesterone (with different content in against a cream containing 30 mg/g of natural Progesterone Gest® commercialized by Emerita) was carried out. Pro-Gesto® is a commercially available cream containing 30 mg/g of original natural Progesterone. Pro-Gesto® has been claimed as a product to help maintain balance in woman's lives and keep them feeling in harmony with their bodies. There are publications of two independent clinical studies showing the results of the effect of Pro-Gesto® percutaneous progesterone body cream on postmenopausal women ("Percutaneous absorption of progesterone in postnenopausal women treated with transdermal estrogen", Kennneth A., Burry MD, Phillip E., Patton, M D., and Kent Hermsmeyer PhD, Portland, Oreg. "Transdermal Progesterone Cream for Vasomotor Symptoms and Post-menopausal Bone Loss", Helene B. Leonetti, MD, Santo Longo, MD, and James N. Anasti, MD.

Study conditions: Franz Vertical Diffusion Cells (Hanson Research Inc.); Pre-shaved abdominal Guinea pig skin was used as experimental model. The receptor solution was 2% w/w polyoxyethylene 20 oleyl ether (Oleth 20), PBS 10 mM, pH 7.4. The experiments were conducted under non-occlusive conditions, at 35° C. and 600 rpm of stirring speed. Prior to the beginning of the study, the skin pieces were mounted in the permeation cells and maintained at 35° C. in contact with the receptor solution. After loading 50 mg of each formulation over the skin, at the indicated times, 1 ml of the receptor solution was withdrawn, and the receptor chamber was immediately refilled with fresh solution.

TABLE XXI

In vitro flux of Progesterone
(Slope of cumulative amount of permeated
drug vs. time between 6 and 24 h.)
Mean ± S.D.
In vitro flux of progesterone ($\mu g/h * cm^2$)

| Example 40 (Pg001-01) (1) | Example 41 (Pg002-01) (2) | Pro-Gest ® (3) |
|---|---|---|
| 3.29 ± 0.48 | 2.23 ± 0.51 | 0.58 ± 0.29 |

(1) Contains 1.0% w/w of Natural Progesterone.
(2) Contains 2.0% w/w of Natural Progesterone.
(3) Contains 3.0% w/w of Natural Progesterone.

TABLE XXII

Progesterone in vitro permeation

Progesterone Cumulative Amount ($\mu g/cm^2$), Mean ± SD

| Time (h) | Example 40 (Pg001-01) | Example 41 (Pg002-01) | Pro-Gest ® |
|---|---|---|---|
| 0 | 0 | 0 | 0 |
| 6 | 20.86 ± 5.66 | 21.51 ± 7.41 | 1.96 ± 1.50 |
| 12 | 40.42 ± 10.87 | 43.34 ± 12.88 | 6.29 ± 2.02 |
| 18 | 64.56 ± 14.95 | 55.44 ± 14.95 | 9.95 ± 3.79 |
| 24 | 78.54 ± 13.69 | 61.98 ± 16.69 | 12.43 ± 4.07 |

According to these results, a Combi Gel™ Progesterone using the invention herein described is considered highly feasible.

Group B: BENZODIAZEPINES

6) Combi Gel™ Alprazolam

I. Alprazolam Transdermal System

In vitro studies were performed in order to evaluate the effect of permeation enhancers on alprazolam permeation profile. After that, a Combi Gel Alprazolam containing 1.0% w/w of Alprazolam was compared in an in vitro study against Combi Gel NETA already described in order to theoretically evaluate the feasibility of the Alprazolam gel.

Finally, a bioavailability study was performed.

A) In vitro results:

The following tables and graphic intend to illustrate the behavior of Alprazolam in terms of permeability when some of the permeation enhancers herein disclosed are present in a propylene glycol solution containing 1.0% w/w of the active drug.

TABLE XXIII

ALPRAZOLAM PERMEATED [$\mu g/cm^2$]

| Time (h) | Alps001 | Alps002 (LA) | Alps003 (OA) | Alps004 (OAL) | Alps009 (LAOL) |
|---|---|---|---|---|---|
| 24 | 5.40 | 245.32 | 300.06 | 159.05 | 302.72 |

LA: contains Lauric Acid
OA: contains Oleic Acid
OAL: contains Oleyl Alcohol
LAOL: contains Lauryl Alcohol It is clearly advisable the effect of the addition of the permeation enhancers to a solution containing Alprazolam as active agent. With the extremely low cumulative amount value obtained with the solution without containing permeation enhancers, one can expect very low rate of permeability for this active drug, nevertheless, the addition of the permeation enhancers clearly increase many times the flux of active drug permeated.

B) Bioavailabilty Study of Combi Gel™ Alprazolam (Experimental Protocol EC008)

Aim

The objective of the study was to evaluate the bioavailability of alprazolam after daily application of an optimized Combi Gel Alprazolam, during 7 days in 4 adult healthy volunteers.

Study Design

Open labeled, bioavailability study.
Drug Studied: Alprazolam
Product in development: Combi Gel™ Alprazolam
Manufactured by: Permatec Laboratorios SA.
Lot.No: Alg004-03 (same formulation as Example 23)
Pharmaceutical Dosage Form: Gel.
Route: Transdermal
Volunteers: A total of 4 healthy volunteers were selected. All of them completed the study.
Treatment: A single daily dose of 2.0 g of Combi Gel® Alprazolam was applied on the shoulders (one gram on a 400 cm2 area of each shoulder) during 7 days.
Biological sampling schedule: Venous blood samples were collected immediately prior to (basal value) and at 1, 3, 6, 12, 24, 72, 73, 75, 78, 84, 96, 144, 145, 147, 150, 156 y 168 h after the first application of gel.
Analytical assay method: Alprazolam plasma levels were assayed using HPLC.

TABLE XXIV

Plasma Levels of Alprazolam (ng/ml)

Time (h)

| | 0 | 1 | 3 | 6 | 12 | 24 | 72 | 73 | 75 | 78 | 84 | 96 | 144 | 145 | 147 | 150 | 156 | 168 |
|---|---|---|---|---|---|---|---|---|---|---|---|---|---|---|---|---|---|---|
| Mean | 0.4 | 0.4 | 0.4 | 0.4 | 0.4 | 0.8 | 5.1 | 5.0 | 4.6 | 4.5 | 5.5 | 7.0 | 6.1 | 6.1 | 6.6 | 6.2 | 7.5 | 7.8 |
| SEM | — | — | — | — | — | 0.4 | 0.8 | 0.9 | 0.7 | 0.8 | 1.2 | 1.0 | 1.6 | 1.7 | 1.7 | 2.1 | 1.4 | 1.3 |

These results show that Combi Gel Alprazolam reached the therapeutic plasmatic levels (between 2-10 ng/ml) described in the literature for a single oral dose of 1 mg Alprazolam (J. Clin. Pharmacol. 1989;29:543-549, Pharmacokinetics and Pharamacodynamics of Alprazolam Following Single and Multiple Oral Doses of a Sustained-Release Formulation). Furthermore, utilizing the invention means herein claimed, it is possible to achieve sustained plasmatic levels avoiding "peaks and valleys" with only one daily application of Combi Gel Alprazolam.

II. Alprazolam Transmucosal (Buccal) System

A) An In vitro permeation study was performed in order to evaluate the influence of the addition of the invention means, on the active drug permeation profile. A Combi Gel Alprazolam able to be administered by the buccal mucosa, was tested. A Combi Gel Alprazolam containing 0.5% w/w of the active drug and the invention herein described was compared against a 0.5% w/w Alprazolam Gel without using the invention.

Study conditions: Franz Vertical Diffusion Cells (Hanson Research Inc.); Hamster cheek pouch was used as experimental model. The receptor solution was 2% w/w polyoxyethylene 20 oleyl ether (Oleth 20), PBS 10 mM, pH 7.4. The experiments were conducted under occlusive conditions, at 37° C. and 600 rpm of stirring speed. 200 mg of each formulation were loaded per cell. One sample of receptor solution was taken at 0.5 h and analyzed for alprazolam content.

Results

TABLE XXV

Alprazolam in vitro transmucosal permeation

| | Alprazolam Cumulative Amount (μg/cm2), Mean ± SD | |
|---|---|---|
| Time (h) | Example 27 (Alg008-01) (1) | Example 29 (Alg010-01) (2) |
| 0 | 0 | 0 |
| 0.5 | 6.43 ± 3.59 | 0.63 ± 0.47 |

(1) 0.5% w/w Alprazolam with the invention (2) 0.5% w/w Alprazolam without the invention B) An In vivo Comparative Bioavailability Study in Rabbits Was Also Performed (EA 005/99)

Study Design

An Alprazolam Buccal Gel developed by Permatec Lab. SA was compared against one marketed alprazolam pill. In the first period of the study the animals (3 adult female rabbits, weighing around 2 Kg) were given one pill containing 1.0 mg of alprazolam. In the second period the same animals received one dose of 200 mg of Alprazolam Buccal Gel (containing 1.0 mg of Alprazolam). Blood samples were taken at the time points indicated in the table and graphic. Alprazolam was analyzed by HPLC.

Results

TABLE XXVI

Alprazolam pill

Alprazolam serum levels (ng/ml)

| Time (h) | Rabbit 1 | Rabbit 2 | Rabbit 3 | Mean serum (ng/ml) | SEM serum (ng/ml) |
|---|---|---|---|---|---|
| 0 | 0 | 0 | 0 | 0 | 0 |
| 0.5 | 154.86 | 119.95 | 196.33 | 157.05 | 22.10 |
| 1 | 159.68 | 141.14 | 186.42 | 162.41 | 13.16 |
| 1.5 | 150.95 | 117.00 | N.A. | 133.98 | 13.88 |
| 2 | 167.46 | 143.01 | 158.09 | 156.19 | 7.13 |

N.A. not available

TABLE XXVII

Alprazolam Gel

Alprazolam serum levels (ng/ml)

| Time (h) | Rabbit 1 | Rabbit 2 | Rabbit 3 | Mean Serum (ng/ml) | SEM serum (ng/ml) |
|---|---|---|---|---|---|
| 0 | 0 | 0 | 0 | 0 | 0 |
| 0.5 | 237.22 | 212.62 | 142.55 | 197.46 | 28.39 |
| 1 | 195.45 | 228.24 | 160.54 | 194.74 | 19.57 |
| 1.5 | 189.23 | 317.11 | 197.82 | 234.72 | 41.32 |
| 2 | 182.12 | 218.43 | 208.73 | 203.09 | 10.87 |

These results clearly show that the invention herein disclosed included in a buccal gel, promotes higher serum levels of Alprazolam than a pill administered perorally; As demonstrated by all the results presented before, comparatives in vitro study against reference products (i.e. Combi Gel NETA) allow us to predict the feasibility of the intended project.

For that reason, the groups of drugs described below, were evaluated on in vitro tests against a reference product and concluded to be feasible to be administered by transdermal or transmucosal route using the invention herein described.

Group C: Antihypothyroid

7) Combi Gel™ L-Tiroxine

A) An In vitro permeation study was performed in order to evaluate the influence of the addition of the invention means, on L-Tiroxine permeation profile. Thus, solutions of the active drug, with and without the addition of the invention means, were in vitro tested.

Study conditions: Franz Vertical Diffusion Cells (Hanson Research Inc.); Pre-shaved abdominal Guinea pig skin was used as experimental model. The receptor solution was 2% w/w polyoxyethylene 20 oleyl ether (Oleth 20), PBS 10 mM, pH 7.4. The experiments were conducted under occlusive conditions, at 37° C. and 600 rpm of stirring speed 2 ml of each formulation was loaded per cell. One sample of receptor solution was taken at different time points.

Results

TABLE XXVIII

In vitro flux of L-Tiroxine.
(Slope of cumulative amount of permeated
drug vs. time between 6 and 24 h.)
Mean ± S.D.
In vitro flux of L-Tiroxine
($\mu$g/h * cm$^2$)

| Example 31 (T4s005-02) (1) | Example 32 (T4s006-01) (2) |
|---|---|
| 6.44 ± 0.91 | 0.26 ± 0.08 |

(1) Contains 0.40% w/w of L-Tiroxine with the invention.
(2) Contains 0.40% w/w of L-Tiroxine without the invention.

TABLE XXIX

L-Tiroxine in vitro permeation

L-Tiroxine Cumulative Amount
($\mu$g/cm$^2$), Mean ± SD

| Time (h) | Example 31 (T4s005-01) (1) | Example 32 (T4s005-01) (2) |
|---|---|---|
| 0 | 0 | 0 |
| 6 | 61.19 ± 21.39 | 0.00 ± 0.00 |
| 12 | 115.21 ± 25.12 | 0.30 ± 0.28 |
| 18 | 149.89 ± 20.30 | 1.91 ± 0.96 |
| 24 | 178.36 ± 27.40 | 4.65 ± 1.31 |

These results clearly shown a significant increment in the cumulative amount permeated of L-Tiroxine when the invention is present in the formulation (about 24 times at 24 hours).

Then, we can conclude that a formulation to administer the antihypotiroid drug at an adequate permeation rate could be achieved by using the present invention.

Group D: Antihypertensives/Calcium Channel Blockers

8) Combi Gel™ Amlodipine

A) In vitro permeation studies were performed in order to evaluate the influence of the addition of the invention means, on Amlodipine Besylate and Amlodipine (base form) permeation profile. Thus, solutions of the active drugs, with and without the addition of the invention means, were in vitro tested.

Study conditions: Franz Vertical Diffusion Cells (Hanson Research Inc.); Pre-shaved abdominal Guinea pig skin was used as experimental model. The receptor solution was 2% w/w polyoxyethylene 20 oleyl ether (Oleth 20), PBS 10 mM, pH 7.4. The experiments were conducted under occlusive conditions, at 35° C. and 600 rpm of stirring speed. 3 ml of each formulation was loaded per cell. One sample of receptor solution was taken at different time points.

Results

TABLE XXX

Amlodipine and Amlodipine Besylate in vitro permeation
Cumulative Amounts ($\mu$g/cm$^2$), Mean ± SD

| Time (h) | Example 39 (AmBss002-01) (1) | Example 37 (AmBss001-01) (2) | Example 38 (Ams002-01) (3) | Example 36 (Ams001-01) (4) |
|---|---|---|---|---|
| 0 | 0.00 | 0.00 | 0.00 | 0.00 |
| 24 | 44.61 ± 18.59 | 0.54 ± 0.10 | 963.13 ± 588.62 | 4.35 ± 1.51 |

(1) Contains 1.00% w/w of Amlodipine Besylate with the additon of the invention means
(2) Contains 1.00% w/w of Amlodipine Besylate without the invention means
(3) Contains 1.00% w/w of Amlodipine with addition of the invention means
(4) Contains 1.00% w/w of Amlodipine without the invention means These results clearly shown a very significant increment in the cumulative amount permeated of both Amlodipine forms (base and Besylate) when the invention is present in the formulation (about 85 times for the Besylate and more than 450 times for the base). The enhancement effect is clearly greater for the base form.

Then we can conclude that a formulation to administer the antihypertensive agent at an adequate permeation rate could be achieved by using the present invention.

What is claimed is:

1. A pharmaceutical composition in the form of a solution, cream, lotion, spray, ointment, gel, aerosol, tablet, suppository or patch device for transdermal or transmucosal administration of alprazolam to a subject, comprising as a permeation enhancing mixture:
   a fatty component in an amount of 0.1% to 20% by weight and comprising a saturated fatty alcohol of formula $CH_3$—$(CH_2)_n$—$CH_2OH$, or an unsaturated fatty alcohol of formula $CH_3(C_nH_{2(n-1)})$—OH, wherein n is an integer of between 8 and 22; and
   a vehicle comprising a monoalkylether of diethyleneglycol, a $C_1$-$C_4$ alkanol, a polyalcohol, and water.

2. The pharmaceutical composition of claim 1, wherein the polyalcohol is a glycol, the alkanol is ethanol, and the monoalkylether of diethyleneglycol is diethylene glycol monoethylether.

3. The pharmaceutical composition of claim 1 wherein the vehicle comprises 5% to 75% by weight of a $C_1$-$C_4$ alkanol, 0.5% to 50% of a polyalcohol, water, and up to 40% by weight of a monoalkylether of diethyleneglycol, with all weights calculated based on the total weight of the composition and provided that the total weights of the components does not exceed 100%.

4. The pharmaceutical composition of claim 3, wherein the fatty component is present in an amount of 0.1% to 10%, the alkanol is present in an amount of 15% to 65%, the polyalcohol is present in an amount of 3% to 20%, and the monoalkylether of diethyleneglycol is present in an amount of 0.2% to 25%.

5. The pharmaceutical composition of claim 4, wherein the fatty component is present in an amount of 0.2% to 3%, the alkanol is present in an amount of 20% to 55%, the polyalcohol is present in an amount of 4% to 10%, and the monoalkylether of diethyleneglycol is present in an amount of 2% to 8%.

6. The pharmaceutical composition of claim 1, which further comprises a gelling agent in an amount of 0.2 to 3% by weight so that the composition is in the form of a gel.

7. The pharmaceutical composition of claim 6, wherein the gelling agent is a polyacrylic acid or a cellulose compound.

8. The pharmaceutical composition of claim 7, wherein the gelling agent is carbopol, hydroxypropylmethylcellulose, carboxymethylcellulose, ethylhydroxyethylcellulose, hydroxypropylcellulose, hydroxyethylcellulose, polyvinylpyrrolidone, a polyoxyethylene/polyoxypropylene copolymer, polyvinylalcohol, a natural gum, an alginate, or a pectin.

9. The pharmaceutical composition of claim 6, which further comprises a pH regulator in an amount of 0.05% to 2% by weight.

10. The pharmaceutical composition of claim 9, wherein the pH regulator is a tertiary amine or sodium hydroxide.

11. The pharmaceutical composition of claim 1, wherein the fatty component is a saturated or unsaturated fatty alcohol where n is an integer of between 8 and 12, the polyalcohol is a glycol, the alkanol is ethanol, and the monoalkylether of diethyleneglycol is diethylene glycol monoethylether.

12. The pharmaceutical composition of claim 11, wherein the fatty component is dodecanol, the polyalcohol is propylene glycol and the pH regulator is triethanolamine or tromethamine.

13. The pharmaceutical composition of claim 1, which further comprises one or more of a flavor agent, saborizant, sweetener or solubilizant in an amount sufficient to impart desired properties to the composition.

* * * * *